United States Patent [19]

Bruneau et al.

[11] Patent Number: 5,217,969
[45] Date of Patent: Jun. 8, 1993

[54] BENZOXAZINE DERIVATIVES AS INHIBITORS OF LEUKOTRIENES

[75] Inventors: Pierre A. R. Bruneau, Ludes, France; Graham C. Crawley, Kerridge, England

[73] Assignees: Imperial Chemical Industries PLC, London, England; ICI Pharma, Cergy Cedex, France

[21] Appl. No.: 717,510

[22] Filed: Jun. 19, 1991

[30] Foreign Application Priority Data

Jun. 21, 1990 [EP] European Pat. Off. ......... 90401757.1
Jan. 15, 1991 [EP] European Pat. Off. ......... 91400076.5

[51] Int. Cl.[5] .................. A61K 31/535; C07D 265/14; C07D 265/36
[52] U.S. Cl. .................... 514/230.5; 544/63; 544/92; 544/93; 544/94; 544/105
[58] Field of Search .................. 544/105, 63, 92, 93, 544/94; 514/230.5

[56] References Cited

U.S. PATENT DOCUMENTS

| | | | |
|---|---|---|---|
| 3,661,917 | 5/1972 | Kaiser et al. | 546/232 |
| 3,743,737 | 7/1973 | Kaiser et al. | 514/331 |
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,725,619 | 2/1916 | Chakraborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |
| 4,876,346 | 10/1989 | Musser et al. | 546/172 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |

FOREIGN PATENT DOCUMENTS

| | | |
|---|---|---|
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0271287 | 6/1988 | European Pat. Off. . |
| 0349062 | 6/1989 | European Pat. Off. . |

Primary Examiner—John M. Ford
Assistant Examiner—Y. N. Gupta
Attorney, Agent, or Firm—Cushman, Darby & Cushman

[57] ABSTRACT

The invention concerns a bicyclic heterocyclic compound of the formula I $$Q-A^1-X^1-Ar-\underset{R^3}{\underset{|}{\overset{OR^1}{\underset{|}{C}}}}-R^2 \qquad I$$

wherein Q is an optionally substituted 10-membered bicyclic heterocyclic moiety containing 1 or 2 N's and a further O or S heteroatom;
$A^1$ is a direct link to $X^1$ or (1-3C)alkylene;
$X^1$ is oxy, thio, sulphinyl, sulphonyl or imino;
Ar is optionally substituted phenylene or pyridylene;
$R^1$ is (1-4C)alkyl, (3-4C)alkenyl or (3-4C)alkynyl; and
$R^2$ and $R^3$ together form a group of the formula $-A^2-X^2-A^3-$ which, together with the carbon atom to which $A^2$ and $A^3$ are attached, defines a ring having 5 to 7 ring atoms, wherein each of $A^2$ and $A^3$ is (1-3C)alkylene and $X^2$ is oxy, thio, sulphinyl or sulphonyl; or a pharmaceutically-acceptable salt thereof.

The compounds of the invention are inhibitors of the enzyme 5-lipoxygenase.

12 Claims, No Drawings

BENZOXAZINE DERIVATIVES AS INHIBITORS OF LEUKOTRIENES

This invention concerns novel bicyclic heterocyclic compounds and more particularly novel bicyclic heterocyclic compounds which are inhibitors of the enzyme 5-lipoxygenase (hereinafter referred to as 5-LO). The invention also concerns processes for the manufacture of said bicyclic heterocyclic compounds and novel pharmaceutical compositions containing them. Also included in the invention is the use of said bicyclic heterocyclic compounds in the treatment of various inflammatory and/or allergic diseases in which the direct or indirect products of 5-LO catalysed oxidation of arachidonic acid are involved, and the production of new medicaments for such use.

As stated above the bicyclic heterocyclic compounds described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain bicyclic heterocyclic compounds are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a bicyclic heterocyclic compound of the formula I (set out hereinafter) wherein Q is a 10-membered bicyclic heterocyclic moiety containing one or two nitrogen heteroatoms and a further heteroatom selected from oxygen and sulphur, which heterocyclic moiety may optionally bear one or two oxo or thioxo substituents and up to four further substituents selected from halogeno, hydroxy, cyano, amino, (1–4C)alkyl, (1–4C)alkoxy, fluoro-(1–4C)alkyl, (1–4C)alkylamino, di-[(1–4C)alkyl]amino, amino-(1–4C)alkyl, (1–4C)alkylamino-(1–4C)alkyl, di-[(1–4C)alkyl]amino-(1–4C)alkyl, phenyl and phenyl-(1–4C)alkyl, and wherein said phenyl or phenyl-(1–4C)alkyl substituent may optionally bear a substituent selected from halogeno, (1–4C)alkyl and (1–4C)alkoxy;

wherein $A^1$ is a direct link to $X^1$ or is (1–3C)alkylene;
wherein $X^1$ is oxy, thio, sulphinyl, sulphonyl or imino;
wherein Ar is phenylene which may optionally bear one or two substituents selected from halogeno, hydroxy, amino, nitro, cyano, carbamoyl, ureido, (1–4C)alkyl, (1–4C)alkoxy, (1–4C)alkylamino, di-[(1–4C)alkyl]amino, fluoro-(1–4C)alkyl and (2–4C)alkanoylamino; or Ar is pyridylene;
wherein $R^1$ is (1–4C)alkyl, (3–4C)alkenyl or (3–4C)alkynyl; and
wherein $R^2$ and $R^3$ together form a group of the formula $—A^2—X^2—A^3—$ which, together with the carbon atom to which $A^2$ and $A^3$ are attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three substituents, which may be the same or different, selected from hydroxy, (1–4C)alkyl and (1–4C)alkoxy;

or wherein $R^1$ and $R^2$ together form a group of the formula $—A^2—X^2—A^3—$ which, together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three (1–4C)alkyl substituents, and wherein $R^3$ is (1–4C)alkyl, (2–4C)alkenyl or (2–4C)alkynyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for Q when it is a 10-membered bicyclic heterocyclic moiety containing one or two nitrogen heteroatoms and a further heteroatom selected from oxygen and sulphur is, for example, a benzo-fused heterocyclic moiety such as 4H-1,4-benzoxazinyl, 4H-1,4-benzothiazinyl and the corresponding 2,3-dihydro derivatives thereof, 4H-3,1-benzoxazinyl, 4H-3,1-benzothiazinyl and the corresponding 1,2-dihydro derivatives thereof, and 3H-benzo[d]-1,2-oxazinyl, 3H-benzo[d]-1,2-thiazinyl and the corresponding 1,4-dihydro derivatives thereof, or, for example, a pyrido-fused heterocyclic moiety such as 4H-pyrido[3,2-b][1,4]oxazinyl, 4H-pyrido[4,3-b][1,4]oxazinyl, 4H-pyrido[3,2-b][1,4]thiazinyl, 4H-pyrido[4,3-b][1,4]thiazinyl and the corresponding 2,3-dihydro derivatives thereof. The heterocyclic moiety may be attached through any available position including from either of the two rings of the bicyclic heterocyclic moiety and including through an available nitrogen atom. The heterocyclic moiety may bear a suitable substituent such as, for example, a (1–4C)alkyl, di-[(1–4C)alkyl]amino-(1–4C)alkyl, phenyl or phenyl-(1–4C)alkyl substituent on an available nitrogen atom.

Suitable values for substituents which may be present on Q or Ar, or on a phenyl or phenyl-(1–4C)alkyl substituent on Q, include, for example:

| | |
|---|---|
| for halogeno: | fluoro, chloro, bromo and iodo; |
| for (1–4C)alkyl: | methyl, ethyl, propyl, isopropyl, butyl, isobutyl and sec-butyl; |
| for (1–4C)alkoxy: | methoxy, ethoxy, propoxy, isopropoxy and butoxy; |
| for fluoro-(1–4C)alkyl: | fluoromethyl, difluoromethyl, trifluoromethyl, 2-fluoroethyl, 2,2,2-trifluoroethyl and pentafluoroethyl; |
| for (1–4C)alkylamino: | methylamino, ethylamino, propylamino and butylamino; and |
| for di-[(1–4C)alkyl]amino: | dimethylamino, diethylamino and dipropylamino. |

Suitable values for substituents which may be present on Q include, for example:-

| | |
|---|---|
| for amino-(1–4C)alkyl: | aminomethyl, 1-aminoethyl, 2-aminoethyl, 2-aminopropyl and 3-aminopropyl; |
| for (1–4C)alkylamino-(1–4C)alkyl: | methylaminomethyl, 2-methylaminoethyl, 3-methylaminopropyl, ethylaminomethyl and 2-ethylaminoethyl; |
| for di-[(1–4C)alkyl]amino-(1–4C)alkyl: | dimethylaminomethyl, 2-dimethylaminoethyl, 3-dimethylaminopropyl, diethylaminomethyl and 2-diethylaminoethyl; |
| for phenyl-(1–4C)alkyl: | benzyl, phenethyl and 3-phenylpropyl. |

A suitable value for $A^1$ when it is (1–3C)alkylene is, for example, methylene, ethylene or trimethylene.

A suitable value for Ar when it is phenylene is, for example, 1,3-phenylene or 1,4-phenylene.

A suitable value for Ar when it is pyridylene is, for example, 3,5- or 2,6-pyridylene.

A suitable value for a (2–4C)alkanoylamino substituent which may be present on Ar is, for example, acetamido, propionamido or butyramido.

A suitable value for $R^1$ when it is (1–4C)alkyl is, for example, methyl, ethyl, propyl or butyl; when it is (3–4C)alkenyl is, for example, allyl, 2-butenyl or 3-butenyl; and when it is (3–4C)alkynyl is, for example, 2-propynyl or 2-butynyl.

When $R^2$ and $R^3$ together form a group of the formula $-A^2-X^2-A^3-$ which, together with the carbon atom to which $A^2$ and $A^3$ are attached, defines a ring having 5 to 7 ring atoms then a suitable value for $A^2$ or $A^3$, which may be the same or different, when each is (1–3C)alkylene is, for example, methylene, ethylene or trimethylene. Suitable values for the substituents which may be present on said 5- to 7-membered ring include for example:

| | |
|---|---|
| for (1–4C)alkyl: | methyl, ethyl, propyl, isopropyl, butyl and isobutyl; |
| for (1–4C)alkoxy: | methoxy, ethoxy, propoxy, isopropoxy and butoxy. |

When $R^1$ and $R^2$ together form a group of the formula $-A^2-X^2-A^3-$ which together with the oxygen atom to which $A^2$ is attached and with the carbon atom to which $A^3$ is attached, defines a ring having 5 to 7 ring atoms then a suitable value for $A^2$ or $A^3$, which may be the same or different, when each is (1–3C)alkylene is, for example, methylene, ethylene or trimethylene. Suitable values for the (1–4C)alkyl substituents which may be present on said 5- to 7-membered ring include, for example, methyl, ethyl, propyl, isopropyl and butyl.

A suitable value for $R^3$ when it is (1–4C)alkyl is, for example, methyl, ethyl, propyl or butyl; when it is (2–4C)alkenyl is, for example, vinyl, allyl, 2-butenyl or 3-butenyl; and when it is (2–4C)alkynyl is, for example, ethynyl, 2-propynyl or 2-butynyl.

A suitable pharmaceutically-acceptable salt of a bicyclic heterocyclic compound of the invention is, for example, an acid-addition salt of a bicyclic heterocyclic compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a bicyclic heterocyclic compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, bicyclic heterocyclic compounds of the formula I wherein:

(a) Q is a 10-membered benzo-fused heterocyclic moiety containing one nitrogen heteroatom and a second heteroatom selected from oxygen and sulphur, which heterocyclic moiety may optionally bear one oxo or thioxo substituent and up to four substituents having the meanings defined hereinbefore for further substituents on Q; and $A^1$, $X^1$, Ar, $R^1$, $R^2$ and $R^3$ have any of the meanings defined hereinbefore;

(b) Q is 4H-1,4-benzoxazinyl, 4H-1,4-benzothiazinyl or the corresponding 2,3-dihydro derivatives thereof, which may optionally bear one oxo or thioxo substituent and up to four substituents having the meanings defined hereinbefore for further substituents on Q; and $A^1$, $X^1$, Ar, $R^1$, $R^2$ and $R^3$ have any of the meanings defined hereinbefore;

(c) Q is 2,3-dihydro-4H-1,4-benzoxazinyl, 2,3-dihydro-4H-1,4-benzothiazinyl, 1,2-dihydro-4H-3,1-benzoxazinyl or 2,3-dihydro-4H-pyrido[3,2-b][1,4]oxazinyl, which may optionally bear one oxo or thioxo substituent and up to four substituents having the meanings defined hereinbefore for further substituents on Q; and $A^1$, $X^1$, Ar, $R^1$, $R^2$ and $R^3$ have any of the meanings defined hereinbefore;

(d) Q is 3-oxo-2,3-dihydro-4H-1,4-benzoxazin-2-yl, 3-oxo-2,3-dihydro-4H-1,4-benzoxazin-6-yl or 3-oxo-2,3-dihydro-4H-1,4-benzoxazin-7-yl or the corresponding 3-thioxo derivatives thereof, or 3-oxo-2,3-dihydro-4H-1,4-benzothiazin-2-yl, 3-oxo-2,3-dihydro-4H-1,4-benzothiazin-6-yl or 3-oxo-2,3-dihydro-4H-1,4-benzothiazin-7-yl or the corresponding 3-thioxo derivatives thereof, which heterocyclic moiety may optionally bear up to four substituents having the meanings defined hereinbefore for further substituents on Q; and $A^1$, $X^1$, Ar, $R^1$, $R^2$ and $R^3$ have any of the meanings defined hereinbefore;

(e) Q is 3-oxo-2,3-dihydro-4H-1,4-benzoxazin-6-yl or 3-oxo-2,3-dihydro-4H-1,4-benzoxazin-7-yl or the corresponding 3-thioxo derivatives thereof, 3-oxo-2,3-dihydro-4H-1,4-benzothiazin-6-yl or 3-oxo-2,3-dihydro-4H-1,4-benzothiazin-7-yl or the corresponding 3-thioxo derivatives thereof, 2-oxo-1,2-dihydro-4H-3,1-benzoxazin-6-yl or 2-oxo-1,2-dihydro-4H-3,1-benzoxazin-7-yl or the corresponding 2-thioxo derivatives thereof, or 3-oxo-2,3-dihydro-4H-pyrido[3,2-b][1,4]oxazin-6-yl or 3-oxo-2,3-dihydro-4H-pyrido[3,2-b][1,4]oxazin-7-yl or the corresponding 3-thioxo derivatives thereof, which heterocyclic moiety may optionally bear up to four substituents having the meanings defined hereinbefore for further substituents on Q; and $A^1$, $X^1$, Ar, $R^1$, $R^2$ and $R^3$ have any of the meanings defined hereinbefore;

(f) $A^1$ is a direct link to $X^1$, and $X^1$ is oxy, thio, sulphinyl or sulphonyl; and Q, Ar, $R^1$, $R^2$ and $R^3$ have any of the meanings defined hereinbefore;

(g) $A^1$ is methylene and $X^1$ is oxy, thio, sulphinyl or sulphonyl; and Q, Ar, $R^1$, $R^2$ and $R^3$ have any of the meanings defined hereinbefore;

(h) Ar is 1,3-phenylene or 1,4-phenylene which may optionally bear one or two substituents selected from fluoro, chloro, hydroxy, amino, nitro, ureido, methyl, methoxy, methylamino, dimethylamino, trifluoromethyl and acetamido; and Q, $A^1$, $X^1$, $R^1$, $R^2$ and $R^3$ have any of the meanings defined hereinbefore;

(i) Ar is 3,5-pyridylene; and Q, $A^1$, $X^1$, $R^1$, $R^2$ and $R^3$ have any of the meanings defined hereinbefore;

(j) $R^1$ is methyl, ethyl, allyl or 2-propynyl; and Q, $A^1$, $X^1$, Ar, $R^2$ and $R^3$ have any of the meanings defined hereinbefore;

(k) $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which may be the same or different, each is methylene, ethylene or trimethylene and $X^2$ is oxy, and which ring may bear one or two substituents selected from hydroxy, methyl, ethyl, propyl, methoxy and ethoxy; and Q, $A^1$, $X^1$, Ar and $R^1$ have any of the meanings defined hereinbefore; or (l) $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 to 7 ring atoms, wherein $A^2$ and $A^3$, which may be the same or different, each is methylene or ethylene and $X^2$ is oxy, and which ring may bear one, two or three substituents selected from methyl, ethyl and propyl, and $R^3$ is methyl or ethyl; and Q, $A^1$, $X^1$ and Ar have any of the meanings defined hereinbefore;

or a pharmaceutically-acceptable salt thereof.

A preferred compound of the invention comprises a bicyclic heterocyclic compound of the formula I wherein Q is 4H-1,4-benzoxazinyl, 4H-1,4-benzothiazinyl or the corresponding 2,3-dihydro derivatives thereof, which may optionally bear one oxo or thioxo substituent and up to four substituents selected from fluoro, chloro, bromo, hydroxy, cyano, amino, methyl, ethyl, propyl, methoxy, trifluoromethyl, 2-fluoroethyl, 2,2,2-trifluoroethyl, 2-methylaminoethyl, 2-dimethylaminoethyl, phenyl and benzyl, and wherein said phenyl or benzyl substituent may optionally bear a substituent selected from chloro, methyl and methoxy;

$A^1$ is a direct link to $X^1$ or is methylene;

$X^1$ is oxy, thio, sulphinyl or sulphonyl;

Ar is 1,3-phenylene or 1,4-phenylene which may optionally bear one or two substituents selected from fluoro, chloro, hydroxy, amino, nitro, ureido, methoxy, dimethylamino, trifluoromethyl and acetamido; or Ar is 3,5-pyridylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl, ethyl, propyl, methoxy and ethoxy;

or $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 or 6 ring atoms, wherein $A^2$ is methylene, $A^3$ is methylene or ethylene, and $X^2$ is oxy, and which ring may bear one, two or three substituents selected from methyl, ethyl and propyl, and $R^3$ is methyl or ethyl;

or a pharmaceutically-acceptable salt thereof.

A further preferred compound of the invention comprises a bicyclic heterocyclic compound of the formula I wherein Q is 3-oxo-2,3-dihydro-4H-1,4-benzoxazin-7-yl or 3-oxo-2,3-dihydro-4H-1,4-benzothiazin-7-yl which may optionally bear one, two or three substituents selected from fluoro, chloro, methyl, ethyl, propyl, 2-fluoroethyl, 2-dimethylaminoethyl, phenyl and benzyl;

$A^1$ is a direct link to $X^1$, or is methylene;

$X^1$ is oxy, thio, sulphinyl or sulphonyl;

Ar is 1,3-phenylene or 1,4-phenylene which may optionally bear one or two substituents selected from fluoro, hydroxy, amino, nitro, ureido, methoxy, dimethylamino, trifluoromethyl and acetamido; or Ar is 3,5-pyridylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or $R^1$ and $R^2$ together form a group of the formula $-A^2-X^2-A^3-$ which, together with the oxygen atom to which $A^2$ is attached and with the carbon atom to which $A^3$ is attached, defines a ring having 5 ring atoms, wherein $A^2$ is methylene, $A^3$ is methylene, and $X^2$ is oxy, and which ring may bear one, two or three substituents selected from methyl and ethyl, and $R^3$ is methyl or ethyl;
or a pharmaceutically-acceptable salt thereof.

A further preferred compound of the invention comprises a bicyclic heterocyclic compound of the formula I wherein Q is 3-oxo-2,3-dihydro-4H-1,4-benzoxazin-7-yl or 3-oxo-2,3-dihydro-4H-1,4-benzothiazin-7-yl, or the corresponding 4-methyl derivatives thereof, which may optionally bear one or two substituents selected from methyl and ethyl;
$A^1$ is a direct link to $X^1$, or is methylene;
$X^1$ is oxy, thio, sulphinyl or sulphonyl;
Ar is 1,3-phenylene which may optionally bear one or two substituents selected from fluoro, methoxy and trifluoromethyl;
$R^1$ is methyl, ethyl or allyl; and
$R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl, ethyl, propyl and methoxy; or a pharmaceutically-acceptable salt thereof.

A further preferred compound of the invention comprises a bicyclic heterocyclic compound of the formula I wherein Q is 4-methyl-3-oxo-2,3-dihydro-4H-1,4-benzoxazin-7-yl or 4-methyl-3-oxo-2,3-dihydro-4H-1,4-benzothiazin-7-yl, or the corresponding 2,2-dimethyl derivatives thereof;
$A^1$ is methylene;
$X^1$ is oxy;
Ar is 1,3-phenylene or 5-fluoro-1,3-phenylene;
$R^1$ is methyl; and
$R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;
or a pharmaceutically-acceptable salt thereof.

A further preferred compound of the invention comprises a bicyclic heterocyclic compound of the formula I wherein Q is 3-oxo-2,3-dihydro-4H-1,4-benzoxazin-6-yl, 3-oxo-2,3-dihydro-4H-1,4-benzoxazin-7-yl, 3-thioxo-2,3-dihydro-4H-1,4-benzoxazin-7-yl, 2-oxo-1,2-dihydro-4H-3,1-benzoxazin-6-yl, 3-oxo-2,3-dihydro-4H-1,4-benzothiazin-7-yl or 3-oxo-2,3-dihydro-4H-pyrido[3,2-b][1,4]oxazin7-yl; or the corresponding N-methyl derivatives thereof, which may optionally bear one or two substituents selected from methyl and ethyl;
$A^1$ is a direct link to $X^1$, or is methylene;
$X^1$ is oxy, thio, sulphinyl or sulphonyl;
Ar is 1,3-phenylene which may optionally bear one or two substituents selected from fluoro, methoxy and trifluoromethyl;
$R^1$ is methyl, ethyl or allyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected form methyl, ethyl, propyl and methoxy;
or a pharmaceutically-acceptable salt thereof.

A further preferred compounds of the invention comprises a bicyclic heterocyclic compound of the formula I wherein Q is 4-methyl-3-oxo-2,3-dihydro-4H-1,4-benzoxazin-6-yl, 4-methyl-3-oxo-2,3-dihydro-4H-1,4-benzoxazin-7-yl, 2,2,4-trimethyl-3-oxo-2,3-dihydro-4H-1,4-benzoxazin-7-yl, 4-methyl-3-thioxo-2,3-dihydro-4H-1,4-benzoxazin -7-yl, 1-methyl-2-oxo-1,2-dihydro-4H-3,1-benzoxazin-6-yl or 4-methyl-3-oxo-2,3-dihydro-4H-pyrido[3,2-b][1,4]oxazin-7-yl;
$A^1$ is a direct link to $X^1$, or is methylene;
$X^1$ is oxy or thio;
Ar is 1,3-phenylene or 5-fluoro-1,3-phenylene;
$R^1$ is methyl; and
$R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$:
or a pharmaceutically-acceptable salt thereof.

Specific especially preferred compounds of the invention include, for example, the following bicyclic heterocyclic compounds of the formula I, or pharmaceutically-acceptable salts thereof:

4-[5-fluoro-3-(4-methyl-3-oxo-2,3-dihydro-4H-1,4-benzoxazin-7-ylmethoxy)phenyl]-4-methoxytetrahydropyran, 4-[5-fluoro-3-(2,2,4-trimethyl-3-oxo-2,3-dihydro-4H-1,4-benzoxazin-7-ylmethoxy)phenyl]-4-methoxytetrahydropyran and 4-[5-fluoro-3-(2,2,4-trimethyl-3-oxo-2,3-dihydro-4H-1,4-benzothiazin-7-ylmethoxy)phenyl]-4-methoxytetrahydropyran.

Further especially preferred compounds of the invention include the following bicyclic heterocyclic compounds of the formula I, or pharmaceutically-acceptable salts thereof:

4-[5-fluoro-3-(4-methyl-3-thioxo-2,3-dihydro-4H-1,4-benzoxazin-7-ylthio)phenyl]-4-methoxytetrahydropyran;

4-[5-fluoro-3-(4-methyl-3-oxo-2,3-dihydro-4H-1,4-benzoxazin-7-ylthio)phenyl]-4-methoxytetrahydropyran;

(2S,4R)-4-[5-fluoro-3-(4-methyl-3-oxo-2,3-dihydro-4H-1,4-benzoxazin-7-ylthio)phenyl]-4-methoxy-2-methyltetrahydropyran;

(S)-(+)-4-[5-fluoro-3-(2,4-dimethyl-3-oxo-2,3-dihydro-4H-1,4-benzoxazin-7-ylthio)phenyl]-4-methoxytetrahydropyran and (R)-(−)-4-[5-fluoro-3-(2,4-dimethyl-3-oxo-2,3-dihydro-4H-1,4-benzoxazin-7-ylthio)phenyl]-4-methoxytetrahydropyran.

A compound of the invention comprising a bicyclic heterocyclic compound of the formula I, or a pharmaceutically-acceptable salt thereof, may be prepared by an process known to be applicable to the preparation of structurally-related compounds. Such procedures are provided as a further feature of the invention and are illustrated by the following representative examples in which, unless otherwise stated, Q, $A^1$, $X^1$, Ar, $R^1$, $R^2$ and $R^3$ have any of the meanings defined hereinbefore.

(a) The coupling, preferably in the presence of a suitable base, of a compound of the formula Q—$A^1$—$X^1$—H with a compound of the formula II wherein Z is a displaceable group; provided that, when there is an amino, alkylamino or hydroxy group in Q, Ar, $R^2$ or $R^3$, any amino, alkylamino or hydroxy group may be protected by a conventional protecting group or alternatively any such group need not be protected, whereafter any undesired protecting group in Q, Ar, $R^2$ or $R^3$ is removed by conventional means.

A suitable displaceable group Z is, for example, a halogeno or sulphonyloxy group, for example a fluoro, chloro, bromo, iodo, methanesulphonyloxy or toluene-p-sulphonyloxy group.

A suitable base for the coupling reaction is, for example, an alkali or alkaline earth metal carbonate, (1–4C)alkoxide, hydroxide or hydride, for example sodium carbonate, potassium carbonate, sodium ethoxide, sodium butoxide, sodium hydroxide, potassium hydroxide, sodium hydride or potassium hydride, or an organometallic base such as (1–4C)alkyl-lithium, for example n-butyl-lithium. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)-palladium, cuprous chloride or cuprous bromide.

A suitable protecting group for an amino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula Q—$A^1$—$X^1$—H and of the formula II may be obtained by standard procedures of organic chemistry. The preparation of such starting materials is described within the accompanying non-limiting Examples which are provided for the purpose of illustration only.

Conveniently intermediates of the formula II wherein Z, Ar, $R^1$, $R^2$ and $R^3$ have the meanings defined hereinbefore, may be obtained by way of compounds of the formula Z—Ar—Y, wherein Z and Ar have the meanings defined hereinbefore and Y is, for example, a halogeno, formyl, alkanoyl, nitrile or alkoxycarbonyl group, as illustrated in accompanying Scheme I (set out hereinafter). Thus, for example, in the accompanying non-limiting Examples it is shown how to convert a compound of the formula Z—Ar—Y wherein Y is a halogeno group to a compound of the formula II.

It will also be appreciated that the intermediate of the formula II may conveniently be obtained from the compound of the formula Z—Ar—Y, as defined hereinbefore, by reversing the order of introduction of the groups $R^2$ and $R^3$ which is used in Scheme I.

(b) The alkylation, preferably in the presence of a suitable base as defined hereinbefore, of a compound of the formula III with a compound of the formula Q—$A^1$—Z wherein Z is a displaceable group as defined hereinbefore; provided that, when there is an amino, alkylamino or hydroxy group in Q, Ar, $R^2$ or $R^3$, any amino, alkylamino or hydroxy group may be protected by a conventional protecting group as defined hereinbefore or alternatively any such group need not be protected, whereafter any undesired protecting group in Q, Ar, $R^2$ or $R^3$ is removed by conventional means.

The alkylation reaction is conveniently performed in a suitable inert solvent as defined hereinbefore and at a temperature in the range, for example, 10° to 150° C., conveniently at or near 100° C. The reaction may conveniently be performed in the presence of a suitable catalyst as defined hereinbefore.

The starting materials of the formula Q—$A^1$—Z and of the formula III may be obtained by standard procedures of organic chemistry. The preparation of such starting materials is described within the accompanying non-limiting Examples which are provided for the purpose of illustration only. Alternatively necessary starting materials are obtainable by analogous procedures to those illustrated in accompanying Scheme II (set out hereinafter) or by modifications thereto which are within the ordinary skill of an organic chemist.

A suitable protecting group $R^4$, as employed in Scheme II, is any one of the many such groups known in the art and includes any appropriate protecting group as defined hereinbefore. Examples of such groups are given in Scheme II. The conditions for the introduction and removal of such protecting groups are described in standard textbooks of organic chemistry such as, for example, "Protective Groups in Organic Synthesis" by T W Green (J Wiley and Sons, 1981).

(c) The alkylation, preferably in the presence of a suitable base as defined hereinbefore, of a compound of the formula IV with a compound of the formula $R^1$—Z, wherein $R^1$ and Z have the meanings defined hereinbefore; provided that, when there is an amino, imino, alkylamino or hydroxy group in Q, $X^1$, Ar, $R^2$ or $R^3$ any amino, imino, alkylamino or hydroxy group may be protected by a conventional protecting group or alternatively any such group need not be protected, whereafter any undesired protecting group in Q, $X^1$, Ar, $R^2$ or $R^3$ is removed by conventional means.

A suitable protecting group for an imino group is, for example, any of the protecting groups defined hereinbefore for an amino or alkylamino group.

The tertiary alcohol starting material of the formula IV may be obtained by standard procedures of organic chemistry. Conveniently, and as illustrated in accompanying Scheme III (set out hereinafter), intermediates of the formulae Q—$A^1$—$X^1$—Ar—Y, wherein Q, $A^1$, $X^1$ and Ar have the meanings defined hereinbefore and Y is, for example, a halogeno, formyl, alkanoyl, nitrile or alkoxycarbonyl group may be utilised in the preparation of the tertiary alcohol starting material of the formula IV.

(d) For the production of those compounds of the formula I wherein $R^1$ and $R^2$ together form a group of the formula —$A^2$—$X^2$—$A^3$—which, together with the oxygen atom to which $A^2$ is attached, defines a ring having 5 to 7 ring atoms and wherein $A^2$, $X^2$ and $A^3$ have the meanings defined hereinbefore, and wherein $R^3$ has the meaning defined hereinbefore; the cyclisation of a compound of the formula V upon reaction with an appropriate aldehyde or ketone, or with a hemiacetal or acetal thereof, or with a compound of the formula Z—$A^2$—Z, wherein Z has the meaning defined hereinbefore; provided that, when there is an amino, imino, alkylamino or hydroxy group in Q, $X^1$ or Ar, any amino, imino, alkylamino or hydroxy group is protected by a conventional protecting group, whereafter any undesired protecting group in Q, $X^1$ or Ar is removed by conventional means.

The cyclisation of a compound of the formula V with an appropriate aldehyde or ketone, or with a hemiacetal or acetal thereof, is conveniently carried out in the presence of a suitable acid. A suitable acid for the cyclisation reaction is, for example, an inorganic acid such as hydrochloric, sulphuric or phosphoric acid, or, for example, an organic acid such as p-toluenesulphonic acid or trifluoroacetic acid. The cyclisation reaction is conveniently performed in a suitable inert solvent or diluent, for example 1,2-dimethoxyethane or tetrahydrofuran. Preferably the reaction is performed using the appropriate aldehyde or ketone, or a hemiacetal or acetal derivative thereof, as both a reactant and diluent. The cyclisation is effected at a temperature in the range, for example, 20° to 150° C., conveniently at or near the boiling point of the diluent or solvent.

The cyclisation of a compound of the formula V with a compound of the formula Z—$A^2$—Z is conveniently carried out in the presence of a suitable base as defined hereinbefore.

The tertiary alcohol starting material of the formula V may be obtained by standard procedures of organic chemistry. Conveniently, and as illustrated in accompanying Scheme IV (set out hereinafter), intermediates of the formula Q—$A^1$—$X^1$—Ar—Y, wherein Q, $A^1$, $X^1$, Ar and Y have the meanings defined hereinbefore, may be utilised in the preparation of the tertiary alcohol starting material of the formula V.

A suitable protecting group $R^4$, as defined hereinbefore, is employed.

(e) For the production of those compounds of the formula I wherein $X^1$ is a sulphinyl or sulphonyl group, wherein $R^2$ and $R^3$ together form a group of the formula —$A^2$—$X^2$—$A^3$— and $X^2$ is a sulphinyl or sulphonyl group or wherein $R^1$ and $R^2$ together form a group of the formula —$A^2$—$X^2$—$A^3$— and $X^2$ is a sulphinyl or sulphonyl group, the oxidation of a compound of the formula I wherein $X^1$ is a thio group, wherein $R^2$ and $R^3$ together form a group of the formula —$A^2$—$X^2$—$A^3$— and $X^2$ is a thio group or wherein $R^1$ and $R^2$ together form a group of the formula —$A^2$—$X^2$—$A^3$— and $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(f) For the production of those compounds of the formula I wherein Ar bears an alkanoylamino substituent, the acylation of a compound of the formula I wherein Ar bears an amino substituent.

A suitable acylating agent is, for example, any agent known in the art for the acylation of amino to acylamino, for example an acyl halide, for example a (2-6-C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C-)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or tert-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(g) For the production of those compounds of the formula I wherein Q bears an alkyl or substituted alkyl substituent on an available nitrogen atom, or wherein Ar bears an alkoxy or substituted alkoxy substituent, the alkylation of a compound of the formula I wherein Q bears a hydrogen atom on said available nitrogen atom, or wherein Ar bears a hydroxy substituent.

A suitable alkylating agent is, for example, any agent known in the art for the alkylation of an available nitrogen atom, or of hydroxy to alkoxy or substituted alkoxy, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(h) For the production of those compounds of the formula I wherein Q bears one or two thioxo substituents, the reaction of a bicyclic heterocyclic compound of the formula I wherein Q bears one or two oxo substituents with a thiation reagent such that each oxo substituent is converted into a thioxo substituent; provided that, when there is an amino, imino, alkylamino or hydroxy group in Q, $X^1$, Ar, $R^2$ or $R^3$ any such group may be protected by a conventional protecting group or alternatively any such group need not be protected, whereafter any undesired protecting group in Q, $X^1$, Ar, $R^2$ and $R^3$ is removed by conventional means.

A suitable thiation reagent is, for example, any agent known in the art for the conversion of an oxo group to a thioxo group such as, for example, 2,4-bis-(4-methoxyphenyl)-1,3-dithia-2,4-diphosphetane-2,4-disulphide (Lawesson's Reagent) or phosphorus pentasulphide. The thiation reaction is generally carried out with the required stoichiometric amount of thiation reagent in order to reduce the risk of damage to other functional groups. In general the reaction is carried out in a suitable solvent or diluent such as toluene, xylene or tetrahydrofuran and at a temperature, for example, at or near the reflux temperature of the solvent or diluent, that is in the range 65° to 150° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae IV and V and these are provided as a further feature of the invention.

As stated previously, the novel compounds of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512–11519). This test provides a measure of the intrinsic inhibitory properties of a test compound against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassays described by Carey and Forder (F. Carey and R. A. Forder, *Prostaglandins, Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(T \times B_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $T \times B_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319–2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431–438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (*British J. Pharmacology*, 1983, 78(1), 67–574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)-f):

Test a):
 $IC_{50}$ in the range, for example, 0.01–30 $\mu M$;

Test b):
 $IC_{50}$ (LTB$_4$) in the range, for example, 0.01–40 $\mu M$
 $IC_{50}$ (TxB$_2$) in the range, for example, 40–200 $\mu M$;

Test c): oral $ED_{50}$(LTB$_4$) in the range, for example, 0.1–100 mg/kg;

Test d):
 $IC_{50}$ (LTC$_4$) in the range, for example, 0.001–1 $\mu M$,
 $IC_{50}$ (PGE$_2$) in the range, for example, 20–1000 $\mu M$;

Test e): inhibition of inflammation in the range, for example, 0.3–100 $\mu g$ intradermally;

Test f): $ED_{50}$ in the range, for example, 0.5–10 mg/kg i.v.;

Test g): oral $ED_{50}$(LTB$_4$) in the range, for example, 0.1–50 mg/kg.

No overt toxicity or other untoward effects are present in tests c), e), f) and/or g) when compounds of the formula I are administered at several muliples of their minimum inhibitory dose or concentration.

Thus, by way of example, the compound 4-[5-fluoro-3-(2,2,4-trimethyl-3-oxo-2,3-dihydro-4H-1,4-benzoxazin-7-ylmethoxy)phenyl]-4-methoxytetrahydropyran has an $IC_{50}$ of 0.05 $\mu M$ against LTB$_4$ in test b), and an oral $ED_{50}$ of 1.5 mg/kg versus LTB$_4$ in test g); the compound 4-[5-fluoro-3-(4-methyl-3-oxo-2,3-dihydro-4H-1,4-benzoxazin-7-ylmethoxy)phenyl]-4-methoxytetrahydropyran has an $IC_{50}$ of 0.04 $\mu M$ against LTB$_4$ in test b), and an oral $ED_{50}$ of 0.4 mg/kg versus LTB$_4$ in test g); the compound 4-[5-fluoro-3-(4-methyl-3-thioxo-2,3-dihydro-4H-1,4-benzoxazin-7-ylthio)phenyl]-4-methoxytetrahydropyran has an $IC_{50}$ of 0.3 $\mu M$ against LTB$_4$ in test b), and an oral $ED_{50}$ of 1.5 mg/kg versus LTB$_4$ in test g); and the compound 4-[5-fluoro-3-(4-methyl-3-oxo-2,3-dihydro-4H-1,4-benzoxazin-7-ylthio)-phenyl]-4-methoxytetrahydropyran has an $IC_{50}$ of 0.05 $\mu M$ against LTB$_4$ in test b), and an oral $ED_{50}$ of 0.15 mg/kg versus LTB$_4$ in test g). In general those compunds of the formula I which are particularly preferred have an $IC_{50}$ of <1 $\mu M$ against LTB$_4$ in test b), and an oral $ED_{50}$ of <100 mg/kg against LTB$_4$ in tests c) and-/or g).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a bicyclic heterocyclic compound of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a bicyclic heterocyclic compound of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a bicyclic heterocyclic compound of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory nonsteroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a bicyclic heterocyclic compound of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:

| THF | tetrahydrofuran; |
|---|---|
| DMSO | dimethylsulphoxide; |
| DMF | N,N-dimethylformamide; |
| DMA | N,N-dimethylacetamide. |

EXAMPLE 1

7-Bromomethyl-4-methyl-3-oxo-2,3-dihydro-4H-1,4-benzoxazine (0.127 g) was added to a mixture of 4-(5-fluoro-3-hydroxyphenyl)-4-methoxytetrahydropyran (0.113 g), potassium carbonate (0.083 g) and DMF (1 ml). The mixture was stirred at ambient temperature for 24 hours. The mixture was partitioned between diethyl ether and water. The organic phase was washed with water, dried (MgSO$_4$) and evaporated. The residue was purified by column chromatography using a 9:1 v/v mixture of methylene chloride and diethyl ether as eluent. There was thus obtained 4-[5-fluoro-3-(4-methyl-3-oxo-2,3-dihydro-4H-1,4-benzoxazin-7-ylmethoxy)-phenyl]-4-methoxytetrahydropyran (0.132 g, 68%), m.p. 87°–89° C. (recrystallised from hexane).

NMR Spectrum (CDCl$_3$, δ values) 1.75–2.0 (m, 4H), 2.98 (s, 3H), 3.37 (s, 3H), 3.65–3.9 (m, 4H), 4.62 (s, 2H), 4.98 (s, 2H), 6.5–7.2 (m, 6H).

The 7-bromomethyl-4-methyl-3-oxo-2,3-dihydro-4H-1,4-benzoxazine used as a starting material was obtained as follows:

Ethyl bromoacetate (20 g) was added to a mixture of 5-methyl-2-nitrophenol (17 g), potassium carbonate (17 g) and acetone (170 ml) and the mixture was heated to 60° C. for 90 minutes. The mixture was cooled to ambient temperature and partitioned between diethyl ether and water. The organic phase was washed in turn with 1N aqueous sodium hydroxide solution, water and brine, dried (MgSO$_4$) and evaporated. The residue was recrystallised from a mixture of diethyl ether and hexane. There was thus obtained ethyl 2-(5-methyl-2-nitrophenoxy)acetate (21.5 g, 82%) m.p. 67° C.

A mixture of the product so obtained, palladium-on-charcoal catalyst (10% w/w, 0.6 g) and ethanol (300 ml) was stirred at ambient temperature under an atmosphere of hydrogen for 1 hour. The mixture was filtered. The filtrate was dissolved in toluene and the solution was heated to 50° C. for 30 minutes. The mixture was evaporated. The residue was triturated under diethyl ether to give 7-methyl-3-oxo-2,3-dihydro-4H-1,4-benzoxazine (14 g, 95%), m.p. 197° C.

A portion (11.4 g) of the product so obtained was added to a stirred suspension of sodium hydride (60% w/w dispersion in mineral oil, 3.36 g; the oil was removed by washing the solid with petroleum ether) in DMF (70 ml) and the mixture was stirred at ambient temperature for 1 hour. Methyl iodide (14.9 g) was added and the mixture was stirred at ambient temperature for 1 hour. The mixture was partitioned between water and a 1:1 v/v mixture of diethyl ether and ethyl acetate. The organic phase was washed with a saturated aqueous sodium thiosulphate solution and with brine, dried (MgSO$_4$) and evaporated. There was thus obtained 4,7-dimethyl-3-oxo-2,3-dihydro-4H-1,4-benzoxazine (11.5 g, 92%), m.p. 107° C.

N-Bromosuccinimide (4.27 g) and benzoyl peroxide (0.1 g) were added in turn to a mixture of the product so obtained (3.54 g) and carbon tetrachloride (50 ml) and the mixture was heated to reflux for 15 minutes. The mixture was cooled to ambient temperature, filtered and evaporated. The residue was purified by column chromatography using initially a 9:1 v/v mixture of methylene chloride and petroleum ether (b.p. 40°-60° C.) and then methylene chloride as eluent. There was thus obtained an oil which crystallised upon trituration under diethyl ether to give the required starting material (0.27 g, 5%).

The 4-(5-fluoro-3-hydroxyphenyl)-4-methoxytetrahydropyran used as a starting material was obtained as follows:

Sodium hydride (50% w/w dispersion in mineral oil, 12.4 g) was added portionwise to a mixture of benzyl alcohol (26.7 ml) and DMA (500 ml) and the mixture was stirred at ambient temperature for 1 hour. 1-Bromo-3,5-difluorobenzene (50 g) was added carefully to control the vigour of the ensuing exothermic reaction. The mixture was stirred at ambient temperature for 2 hours and the solvent was evaporated. The residue was partitioned between methylene chloride and water and the organic phase was washed with water (4×50 ml), dried (MgSO₄) and evaporated. The residue was purified by distillation to give 3-benzyloxy-1-bromo-5-fluorobenzene (41.8 g, 57%), as a colourless liquid (b.p. 124°-130° C. at 0.3 mm Hg).

A solution of a portion (9.7 g) of this product in THF (150 ml) was cooled to −75° C. and n-butyl-lithium (1.6M in hexane, 22 ml) was added dropwise. The mixture was stirred at −75° C. for 1 hour and a solution of tetrahydropyran-4-one (3.47 g) in THF (10 ml) was added dropwise. The mixture was stirred at −75° C. for 1 hour and then allowed to warm to 0° C. A saturated aqueous ammonium chloride solution (50 ml) was added and the organic phase was separated, dried (MgSO₄) and evaporated. The residue was purified by column chromatography using a 1:1 v/v mixture of toluene and ethyl acetate as eluent. There was thus obtained 4-(3-benzyloxy-5-fluorophenyl)-4-hydroxytetrahydropyran (7.4 g, 71%) as an oil.

After appropriate repetition of the above-mentioned reaction the product so obtained (12.1 g) was dissolved in THF (150 ml) and sodium hydride (50% w/w dispersion in mineral oil, 2.11 g) was added portionwise. The mixture was stirred at ambient temperature for 1 hour, cooled in an ice-bath and methyl iodide (3.75 ml) was added dropwise. The mixture was stirred at ambient temperature for 18 hours, 2N aqueous hydrochloric acid (3 drops) was added and the organic solvent was evaporated. The residue was partitioned between ethyl acetate and water. The organic phase was separated, washed with water and with brine, dried (MgSO₄) and evaporated. There was thus obtained 4-(3-benzyloxy-5-fluorophenyl)-4-methoxytetrahydropyran (12.5 g, 99%) as a pale yellow oil which was used without further purification.

A solution of the product so obtained in ethanol (100 ml) was hydrogenated in the presence of 10% palladium-on-charcoal catalyst for 3 hours. The mixture was filtered and the filtrate was evaporated. There was thus obtained 4-[5-fluoro-3-hydroxyphenyl)-4-methoxytetrahydropyran (7.7 g, 86%), m.p. 123°-124° C.

EXAMPLE 2

The procedure described in Example 1 was repeated except that 7-bromomethyl-2,2,4-trimethyl-3-oxo-2,3-dihydro-4H-1,4-benzoxazine was used in place of 7-bromomethyl-4-methyl-3-oxo-2,3-dihydro-4H-1,4-benzoxazine. There was thus obtained 4-[5-fluoro-3-(2,2,4-trimethyl-3-oxo-2,3-dihydro-4H-1,4-benzoxazin-7-ylmethoxy)phenyl]-4-methoxytetrahydropyran in 35% yield, m.p. 118° C.

NMR Spectrum (CDCl₃, δ values) 1.50 (s, 6H), 1.75-2.0 (m, 4H), 2.98 (s, 3H), 3.36 (s, 3H), 3.65-3.95 (m, 4H), 4.98 (s, 2H), 6.95-7.25 (m, 6H).

The 7-bromomethyl-2,2,4-trimethyl-3-oxo-2,3-dihydro-4H-1,4-benzoxazine used as a starting material was obtained as follows:

Methyl 2-bromo-2-methylpropionate (5.43 g) was added to a mixture of 5-methyl-2-nitrophenol (4.59 g), potassium carbonate (4.14 g) and acetone (50 ml) and the mixture was heated to reflux for 90 minutes. As the rate of reaction was slow the bulk of the acetone was evaporated, DMF (25 ml) was added and the mixture was heated to 100° C. for 3 hours and then to 50° C. for 16 hours. The mixture was cooled to ambient temperature and partitioned between dilute aqueous hydrochloric acid and a 1:1 v/v mixture of diethyl ether and ethyl acetate. The organic phase was washed with water, dried (MgSO₄) and evaporated. The residue was purified by column chromatography using methylene chloride as eluent. There was thus obtained methyl 2-methyl-2-(5-methyl-2-nitrophenoxy)propionate (1.2 g, 16%), m.p. 60°-61° C. (recrystallised from hexane).

Using the procedures described in the second to fourth paragraphs of the portion of Example 1 which is concerned with the preparation of 7-bromomethyl-4-methyl-3-oxo-2,3-dihydro-4H-1,4-benzoxazine, the product so obtained was converted into the required starting material in 29% yield.

EXAMPLE 3

The procedure described in Example 1 was repeated except that 7-bromomethyl-2,2,4-trimethyl-3-oxo-2,3-dihydro-4H-1,4-benzothiazine was used in place of 7-bromomethyl-4-methyl-3-oxo-2,3-dihydro-4H-1,4-benzoxazine. There was thus obtained 4-[5-fluoro-3-(2,2,4-trimethyl-3-oxo-2,3-dihydro-4H-1,4-benzothiazin-7-ylmethoxy)phenyl]-4-methoxytetrahydropyran in 51% yield, m.p. 141°-142° C.

NMR Spectrum (CDCl₃, δ values) 1.43 (s, 6H), 1.8-2.1 (m, 4H), 2.98 (s, 3H), 3.46 (s, 3H), 3.75-3.95 (m, 4H), 4.99 (s, 2H), 6.5-7.5 (m, 6H).

The 7-bromomethyl-2,2,4-trimethyl-3-oxo-2,3-dihydro-4H-1,4-benzothiazine used as a starting material was obtained as follows:

Methyl thioglycolate (3.18 g) was added to a mixture of 3-fluoro-4-nitrotoluene (4.65 g), sodium bicarbonate (3 g) and methanol (46 ml) and the mixture was heated to 70° C. for 5 hours. The mixture was cooled to ambient temperature and partitioned between diethyl ether and water. The organic phase was washed with a saturated aqueous sodium bicarbonate solution and with brine, dried (MgSO₄) and evaporated. The residue was recrystallised from a mixture of diethyl ether and hexane to give methyl 2-(5-methyl-2-nitrophenylthio)acetate (6.5 g, 90%), m.p. 74°-75° C.

A mixture of a portion (4 g) of the product so obtained, palladium-on-charcoal (10%, 0.4 g) and methanol (130 ml) was stirred under a pressure of four atmospheres of hydrogen for 5 hours. The mixture was filtered and the filtrate was evaporated. The residue was dissolved in toluene and the solution was heated to reflux for 3.5 hours. The mixture was evaporated and the residual solid was washed with diethyl ether. There was thus obtained 7-methyl-3-oxo-2,3-dihydro-4H-1,4-benzothiazine (2.1 g, 70%), m.p. 207° C.

The product so obtained was dissolved in DMF (5 ml) and added dropwise to a stirred suspension of sodium hydride (60% w/w in oil, 0.64 g, washed with petroleum ether) in DMF (10 ml). The mixture was stirred at ambient temperature for 30 minutes and then cooled in an ice-water bath. Methyl iodide (1.15 ml) was added dropwise and the mixture was stirred for 30 minutes. The mixture was partitioned between diethyl ether and water. The organic phase was washed with water and brine, dried (MgSO$_4$) and evaporated. The residue was purified by column chromatography using a 9:1 v/v mixture of methylene chloride and diethyl ether as eluent. There was thus obtained 4,7-dimethyl-3-oxo-2,3-dihydro-4H-1,4-benzothiazine (2.07 g, 88%), m.p. 84°-86° C.

A portion (1.35 g) of the product so obtained was dissolved in DMF (15 ml). Sodium hydride (60% w/w dispersion in oil, 0.84 g) was added portionwise and the mixture was stirred at ambient temperature for 30 minutes. Methyl iodide (0.69 ml) was added dropwise and the mixture was stirred at ambient temperature for 16 hours. Further portions of sodium hydride dispersion (0.28 g) and methyl iodide (1.38 ml) were added in turn and the mixture was heated to 45° C. for 1 hour. The mixture was partitioned between water and 1:1 v/v mixture of diethyl ether and ethyl acetate. The organic phase was washed with water and with brine, dried (MgSO$_4$) and evaporated. The residue was purified by column chromatography using a 19:1 v/v mixture of methylene chloride and diethyl ether as eluent. There was thus obtained 2,2,4,7-tetramethyl-3-oxo-2,3-dihydro-4H-1,4-benzothiazine (1.02 g, 66%).

Benzoyl peroxide (5 mg) was added to a mixture of a portion (0.22 g) of the product so obtained, N-bromosuccinimide (0.242 g) and carbon tetrachloride (5 ml). The mixture was irradiated with the light from a 250 Watt lamp and heated to 40° C. for 90 minutes. The mixture was cooled to ambient temperature, diethyl ether (5 ml) was added and the mixture was filtered. The filtrate was evaporated to give the required starting material [0.33 g, 78% (70% pure by NMR)] as an oil which was used without further purification.

EXAMPLE 4

A mixture of 6-chloromethyl-4-methyl-3-oxo-2,3-dihydro-4H-1,4-benzoxazine (0.106 g), 4-(5-fluoro-3-hydroxyphenyl)-4-methoxytetrahydropyran (0.113 g), potassium carbonate (0.083 g) and DMF (1 ml) was heated to 80° C. for 3 hours and to 60° C. for a further hour. The mixture was cooled to ambient temperature and partitioned between ethyl acetate and water. The organic phase was washed with water, dried (MgSO$_4$) and evaporated. The residue was purified by column chromatography using a 93:7 v/v mixture of methylene chloride and acetone as eluent. There was thus obtained 4-[5-fluoro-3-(4-methyl-3-oxo-2,3-dihydro-4H-1,4-benzoxazin-6-ylmethoxy)phenyl]-4-methoxytetrahydropyran (0.065 g; 32%), m.p. 124°-131° C.

NMR Spectrum (CDCl$_3$, δ values) 1.8-2.05 (m, 4H), 2.99 (s, 3H), 3.38 (s, 3H), 3.68-3.90 (m, 4H), 4.62 (s, 2H), 5.0 (s, 2H), 6.5-7.25 (m, 6H).

The 6-chloromethyl-4-methyl-3-oxo-2,3-dihydro-4H-1,4-benzoxazine used as a starting material was obtained as follows:

A solution of chloroacetyl chloride (31.2 g) in chloroform (100 ml) was added dropwise to a mixture of 2-aminophenol (25 g), benzylmethylammonium chloride (52.4 g), sodium bicarbonate (77 g) and chloroform (500 ml) which was cooled in an ice-bath. The mixture was stirred for 1 hour and allowed to warm to ambient temperature. The mixture was heated to 55° C. for 5 hours and then stirred at ambient temperature for 16 hours. The mixture was evaporated and the residue was partitioned between ethyl acetate and an aqueous solution of potassium carbonate. The organic phase was washed with dilute aqueous hydrochloric acid and with water, dried (MgSO$_4$) and evaporated. The residue was washed with a mixture of hexane and diethyl ether to leave 3-oxo-2,3-dihydro-4H-1,4-benzoxazine (11 g, 32%) m.p. 172°-173° C.

A portion (5.2 g) of the product so obtained was added portionwise to a stirred suspension of sodium hydride (60% w/w dispersion in mineral oil, 1.66 g; the oil was removed by washing the solid with petroleum ether) in DMF (45 ml) and the mixture was stirred at ambient temperature for 30 minutes. The mixture was cooled in an ice-bath and methyl iodide (2.3 ml) was added dropwise. The mixture was stirred for 1 hour and allowed to warm to ambient temperature. The mixture was poured into water, acidified by the addition of dilute aqueous hydrochloric acid and extracted with ethyl acetate. The organic phase was washed with water, dried (MgSO$_4$) and evaporated. The resultant oil crystallised upon trituration in a 1:9 v/v mixture of diethyl ether and hexane. There was thus obtained 4-methyl-3-oxo-2,3-dihydro-4H-1,4-benzoxazine (4 g, 70%), m.p. 57°-58° C.

A mixture of a portion (0.489 g) of the product so obtained, paraformaldehyde (0.135 g), glacial acetic acid (3 ml) and concentrated hydrochloric acid (3 ml) was heated to 60° C. for 90 minutes. The mixture was cooled to ambient temperature and partitioned between ethyl acetate and water. The organic phase was washed with water, dried (MgSO$_4$) and evaporated. The residue was purified by column chromatography using methylene chloride as eluent. There was thus obtained the required starting material (0.368 g, 58%) as a solid.

EXAMPLE 5

Butyl-lithium (1.6M in hexane, 1 ml) was added dropwise to a mixture of 7-mercapto-4-methyl-3-oxo-2,3-dihydro-4H-1,4-benzoxazine (0.292 g), 4-(3,5-difluorophenyl)-4-methoxytetrahydropyran (0.342 g) and N-methylpyrrolidin-2-one (3.75 ml) which had been cooled in an ice-bath. The mixture was stirred and allowed to warm to ambient temperature. The mixture was heated to 145° C. for 90 minutes, the hexane being distilled out of the reaction mixture. The mixture was cooled to ambient temperature and partitioned between ethyl acetate and water. The organic phase was washed with water and with N aqueous sodium hydroxide solution, dried (MgSO$_4$) and evaporated. The residue was purified by column chromatography using a 15:1 v/v mixture of methylene chloride and diethyl ether as eluent. There was thus obtained 4-[5-fluoro-3-(4-methyl-3-oxo-2,3-dihydro-4H-1,4-benzoxazin-7-ylthio)phenyl]-4-methoxytetrahydropyran (0.202 g, 33%), m.p. 131°-133° C.

NMR Spectrum (CDCl$_3$, δ values) 1.8-2.1 (m, 4H), 2.98 (s, 3H), 3.37 (s, 3H), 3.75-3.95 (m, 4H), 4.63 (s, 2H), 6.76-7.25 (m, 6H).

The 7-mercapto-4-methyl-3-oxo-2,3-dihydro-4H-1,4-benzoxazine used as a starting material was obtained as follows:

A mixture of 5-fluoro-2-nitrophenol (10.05 g), potassium carbonate (10.6 g) and acetone (125 ml) was heated to reflux for 10 minutes. The mixture was cooled to ambient temperature and a solution of ethyl bromoacetate (7.8 ml) in acetone (10 ml) was added dropwise. The mixture was heated to reflux for 2.5 hours. The mixture was evaporated and the residue was partitioned between diethyl ether and water. The organic phase was washed with water, dried (MgSO$_4$) and evaporated. There was thus obtained ethyl 2-(5-fluoro-2-nitrophenoxy)acetate (14.28 g, 92%), m.p. 44°–46° C.

A mixture of ethyl 2-(5-fluoro-2-nitrophenoxy)acetate (11 g), benzylmercaptan (5.2 g), triethylamine (5.08 g) and DMF (50 ml) was stirred and heated to 80° C. for 7 hours. The mixture was cooled, poured into water and acidified by the addition of dilute aqueous hydrochloric acid. The mixture was extracted with diethyl ether. The organic phase was washed with water and with brine, dried (MgSO$_4$) and evaporated to give ethyl 2-(5-benzylthio-2-nitrophenoxy)acetate (10.6 g, 68%) as a solid.

A mixture of a portion (8.68 g) of the product so obtained, stannous chloride dihydrate (*Tet.Let.*, 1984, 839; 28.1 g), ethyl acetate (5 ml) and ethanol (50 ml) was heated to reflux for 30 minutes. The mixture was poured onto ice and a saturated aqueous sodium bicarbonate solution was added. The resultant precipitate was removed by filtration and the filtrate was extracted with ethyl acetate. The organic phase was washed with water and with brine, dried (MgSO$_4$) and evaporated to give 7-benzylthio-3-oxo-2,3-dihydro-4H-1,4-benzoxazine (3.32 g, 49%), m.p. 153°–154° C.

A portion of (2.7 g) of the product so obtained was added to a stirred suspension of sodium hydride (60% w/w dispersion in mineral oil, 0.52 g; the oil was removed by washing the solid dispersion with petroleum ether) in DMF (10 ml) and the mixture was stirred at ambient temperature for 30 minutes. Methyl iodide (2.13 g) was added and the mixture was stirred at ambient temperature for 30 minutes. The mixture was partitioned between diethyl ether and water. The organic phase was washed with water and with brine, dried (MgSO$_4$) and evaporated to give 7-benzylthio-4-methyl-3-oxo-2,3-dihydro-4H-1,4-benzoxazine (2.6 g, 91%) as a solid.

A solution of 3-chloroperbenzoic acid (1.72 g) in chloroform (10 ml) was added dropwise to a solution of a portion (2 g) of the benzoxazine so obtained in chloroform (15 ml) which had been cooled to 0° C. and the mixture was stirred at 0° C. for 4 hours. Calcium hydroxide (0.74 g) was added and the mixture was stirred at ambient temperature for 15 minutes. The mixture was filtered and the filtrate was evaporated to give 7-benzylsulphinyl-4-methyl-3-oxo-2,3-dihydro-4H-1,4-benzoxazine (2.1 g) as a solid which was used without further purification.

Trifluoroacetic acid (4.2 g) was added dropwise to a stirred suspension of a portion (1.5 g) of the benzoxazine so obtained in methylene chloride (45 ml) and the solution so obtained was stirred at ambient temperature for 30 minutes and then heated to reflux for 30 minutes. The mixture was evaporated and the residue was partitioned between ethyl acetate and water. The organic phase was washed with water and with a saturated aqueous sodium bicarbonate solution, dried (MgSO$_4$) and evaporated. The residue was purified by column chromatography using increasingly polar mixtures of methylene chloride and diethyl ether as eluent. There was thus obtained di-(4-methyl-3-oxo-2,3-dihydro-4H-1,4-benzoxazin-7-yl) disulphide (0.68 g, 60%), m.p. 133°–135° C.

After repetition of the preceding step triphenylphosphine (0.576 g) was added to a suspension of the disulphide (0.776 g) in 1,4-dioxane (9 ml). Water (2.5 ml) and concentrated hydrochloric acid (1 drop) were added in turn and the mixture was heated to 50° C. for 1 hour. The mixture was cooled to ambient temperature and partitioned between ethyl acetate and 0.5N aqueous sodium hydroxide solution. The organic phase was washed with water and with brine, dried (MgSO$_4$) and evaporated. There was thus obtained the required starting material (0.425 g, 55%) m.p. 95°–96° C.

The 4-(3,5-difluorophenyl)-4-methoxytetrahydropyran used as a starting material was obtained as follows:

A Grignard reagent was prepared from 3,5-difluorobromobenzene (38.6 g) and magnesium (4.88 g) in a mixture of toluene (100 ml) and THF (50 ml) using the following method. The 3,5-difluorobromobenzene was dissolved in toluene (50 ml) and a portion (aprox. 5%) of the solution was added to a stirred suspension of the magnesium in a mixture of toluene (50 ml) and THF (50 ml). The mixture was stirred at ambient temperature for approximately 40 minutes until the initiation of the exothermic formation of the Grignard reagent was observed. The mixture was cooled in an ice-bath to a temperature in the range 15° to 20° C. while the remainder of the solution of 3,5-difluorobromobenzene was added. The mixture was stirred at ambient temperature for 2 hours.

Tetrahydropyran-4-one (10.69 g) was added over 1 hour to a portion (100 ml) of the Grignard reagent so obtained which was cooled to a temperature in the range 15° to 20° C. The mixture was stirred at ambient temperature for 2 hours. The mixture was cooled in an ice-bath and aqueous hydrochloric acid solution (50% w/v, 25 ml) and brine (30% w/v, 52 ml) were added in turn. The toluene layer was separated and the aqueous layer was extracted with toluene (32 ml). The organic solutions were combined and washed with water (4×32 ml). The solution was evaporated under reduced pressure to a volume of 16.3 ml. There was thus obtained a concentrated (90% w/v) solution of 4-(3,5-difluorophenyl)-4-hydroxytetrahydropyran in toluene. The concentrate was warmed to 60° C. and chlorobenzene (22.25 ml) was added, the temperature being maintained at 60° C. The mixture was allowed to cool to ambient temperature and then cooled in an ice-bath to a temperature in the range 0° to 5° C. The precipitate was isolated and washed with hexane (2×10 ml). There was thus obtained 4-(3,5-difluorophenyl)-4-hydroxytetrahydropyran (12.2 g).

A portion (7.15 g) of the material so obtained was dissolved in N-methylpyrrolidin-2-one (25 ml) and added to a slurry of sodium hydride (60% w/w dispersion in mineral oil; 3.34 g) in N-methylpyrrolidin-2-one (32 ml) which was cooled in an ice-bath to approximately 20° C. The mixture was stirred at this temperature for 30 minutes. Methyl idodide (5.22 g) was dissolved in N-methylpyrrolidin-2-one (2 ml) and added to the mixture. The resultant mixture was warmed to 30° C. and stirred for 2 hours. The mixture was evaporated. There was thus obtained 4-(3,5-difluorophenyl)-4-methoxytetrahydropyran which was used without further purification.

EXAMPLE 6

A solution of potassium peroxymonosulphate (0.115 g) in water (1 ml) was added to a solution of 4-[5-fluoro-3-(4-methyl-3-oxo-2,3-dihydro-4H-1,4-benzoxazin-7-ylthio)phenyl]-4-methoxytetrahydropyran (0.102 g) in a mixture of methylene chloride (1 ml) and chloroform (1 ml) and the resultant mixture was stirred at ambient temperature for 24 hours. The mixture was partitioned between ethyl acetate and water. The organic phase was washed with water, with an aqueous sodium hydrogen sulphite solution and with brine, dried (MgSO$_4$) and evaporated. The residue was purified by column chromatography using increasingly polar mixtures of methylene chloride and diethyl ether as eluent. There was thus obained 4-[5-fluoro-3-(4-methyl-3-oxo-2,3-dihydro-4H-1,4-benzoxazin-7-ylsulphonyl)phenyl]-4-methoxytetrahydropyran (0.066 g, 60%), m.p. 190°–191° C.

NMR Spectrum (CDCl$_3$, δ values) 1.85–2.1 (m, 4H), 2.98 (s, 3H), 3.37 (s, 3H), 3.8–3.95 (m, 4H), 4.66 (s, 2H), 7.0–7.8 (m, 6H).

EXAMPLE 7

2,4-Bis(4-methoxyphenyl)-1,3-dithia-2,4-diphosphetane-2,4-disulphide (Lawesson's Reagent, 0.121 g) was added portionwise to a solution of 4-[5-fluoro-3-(4-methyl-3-oxo-2,3-dihydro-4H-1,4-benzoxazin-7-ylthio)phenyl]-4-methoxytetrahydropyran (0.12 g) in toluene (10 ml) and the mixture was stirred and heated to reflux for 15 minutes. The mixture was evaporated and the residue was purified by column chromatography using a 19:1 v/v mixture of methylene chloride and diethyl ether as eluent. There was thus obtained 4-[5fluoro-3-(4-methyl-3-thioxo-2,3-dihydro-4H-1,4-benzoxazin-7-ylthio)phenyl]-4-methoxytetrahydropyran (0.089 g, 70%), m.p. 125°–127° C.

NMR Spectrum (CDCl$_3$, δ values) 1.65–2.05 (m 4H), 2.92 (s, 3H), 3.6–3.8 (m, 7H), 4.85 (s, 2H), 6.65–7.15 (m, 6H).

EXAMPLE 8

A mixture of 6-iodo-1-methyl-2-oxo-1,2-dihydro-4H-3,1-benzoxazine (0.289 g), 4-(3-mercaptophenyl)-4-methoxytetrahydropyan (0.324 g), potassium carbonate (0.225 g), cuprous chloride (0.03 g) and DMF (3 ml) was heated to 140° C. for 3 hours. The mixture was cooled to ambient temperature and partitioned between ethyl acetate and water. The organic phase was washed with water and with brine, dried (MgSO$_4$) and evaporated. The residue was purified by column chromatography using a 1:1 v/v mixture of toluene and ethyl acetate as eluent. There was thus obtained 4-methoxy-4-[3-(1-methyl-2-oxo-1,2-dihydro-4H-3,1-benzoxazin-6ylthio)phenyl]tetrahydropyran (0.164 g, 43%) as an oil.

NMR Spectrum (CDCl$_3$, δ values) 1.85–2.05 (m, 4H), 2.95 (s, 3H), 3.4 (s, 3H), 3.75–3.90 (m, 4H), 5.15 (s, 2H), 6.9 (d, 1H), 7.1–7.4 (m, 6H).

The 6-iodo-1-methyl-2-oxo-1,2-dihydro-4H-3,1-benzoxazine used as a starting material was obtained as follows:

Phosgene (20% w/v in toluene, 54 ml) was added dropwise to a stirred mixture of 2-aminobenzyl alcohol (12.32 g), triethylamine (27.9 ml) and toluene (500 ml) which was cooled in an ice-bath to approximately 15° C. The mixture was stirred at ambient temperature for 2 hours and then heated to 85° C. for 2 hours. The mixture was poured into water (500 ml) and filtered. The solid (4.6 g) was dried. The organic phase of the filtrate was washed with water, dried (MgSO$_4$) and evaporated. The residue and the solid which had previously been filtered off were purified by column chromatography using a 7:3 v/v mixture of toluene and ethyl acetate as eluent. There was thus obtained 2-oxo-1,2-dihydro-4H-3,1-benzoxazine (7.8 g, 52%), m.p. 115°–116° C.

Sodium hydride (55% w/w dispersion in mineral oil, 0.32 g) was added portionwise to a mixture of a portion (1 g) of the benzoxazine so obtained and DMF (25 ml) which had been cooled to approximately 3° C. and the mixture was stirred at ambient temperature for 1 hour. Methyl iodide (1 ml) was added and the mixture was stirred at ambient temperature for 16 hours. The mixture was partitioned between ethyl acetate and water. The organic phase was washed with water and with brine, dried (MgSO$_4$) and evaporated. The residue was purified by column chromatography using a 7:3 v/v mixture of toluene and ethyl acetate as eluent. There was thus obtained 1-methyl-2-oxo-1,2-dihydro-4H-3,1-benzoxazine (0.8 g, 73%) as an oil.

NMR Spectrum (CDCl$_3$, δ values) 3.38 (s, 3H), 5.20 (s, 2H), 6.92–7.39 (m, 4H).

A mixture of a portion (0.77 g) of the benzoxazine so obtained, concentrated sulphuric acid (0.5 ml) and glacial acetic acid (4 ml) was stirred at ambient temperature and iodic acid (0.276 g) and iodine (0.6 g) were added in turn. The resultant mixture was heated to 95°–100° C. for 2 hours. The mixture was cooled to ambient temperature, methylene chloride (10 ml) was added and the mixture was neutralised by the addition of a saturated aqueous sodium bicarbonate solution. The mixture was washed with a saturated aqueous sodium sulphite solution and with brine, dried (MgSO$_4$) and evaporated. The residue was purified by column chromatography using a 4:1 v/v mixture of toluene and ethyl acetate as eluent. There was thus obtained the required starting material (0.45 g, 33%) as a solid.

NMR Spectrum (CDCl$_3$, δ values) 3.35 (s, 3H), 5.15 (s, 2H), 6.7 (d, 1H), 7.45 (d, 1H), 7.65 (m, 1H).

The 4-(3-mercaptophenyl)-4-methoxytetrahydropyran used as a starting material was obtained as follows:

A solution of 1,3-dibromobenzene (23.8 g) in THF (120 ml) was cooled to −78° C. under an atmosphere of argon and n-butyl-lithium (1.6M in hexane, 62.5 ml) was added dropwise. The mixture was stirred at −78° C. for 30 minutes and a solution of tetrahydropyran-4-one (10 g) in THF (40 ml) was added. The resultant suspension was stirred at −78° C. for 1 hour, allowed to warm to ambient temperature and then stirred for 30 minutes. The mixture was poured into brine (250 ml) and extracted with diethyl ether. The organic phase was dried (MgSO$_4$) and evaporated. The residue was triturated under hexane and the resultant solid (16.8 g) was filtered off.

A solution of the product so obtained in DMF (100 ml) was added dropwise to a slurry of sodium hydride (60% w/w dispersion in mineral oil; 5.25 g) in DMF (10 ml) and the mixture was stirred at ambient temperature for 90 minutes. Methyl iodide (36.5 g) was added and the mixture was stirred at ambient temperature for 16 hours. Ethanol (2 ml) and water (500 ml) were added in turn and the mixture was extracted with diethyl ether (3×200 ml). The combined extracts were washed with water, dried (MgSO$_4$) and evaporated. The residue was purified by column chromatrography using increasingly polar mixtures of hexane and ethyl acetate as eluent. There was thus obtained 4-(3-bromophenyl)-4-methoxytetrahydropyran (12 g, 44%) as a solid.

NMR Spectrum (CDCl₃, δ values) 1.88–2.1 (m, 4H), 3.0 (s, 3H), 3.78–3.95 (m, 4H), 7.2–7.35 (m, 2H), 7.42 (m, 1H), 7.55 (m, 1H).

A solution of a portion (1 g) of the product so obtained in THF (4 ml) was cooled to −80° C. under an atmosphere of argon and n-butyl lithium (1.6M in hexane, 2.4 ml) was added dropwise. The mixture was stirred at −80° C. for 30 minutes, sulphur (0.12 g) was added and the mixture was stirred at −80° C. for a further 30 minutes. Water (10 ml) was added and the mixture was allowed to warm to ambient temperature. The mixture was extracted with diethyl ether (10 ml). The aqueous phase was acidified to pH4 by the addition of dilute aqueous hydrochloric acid solution and extracted with diethyl ether (2×10 ml). The combined organic extracts were dried (MgSO₄) and evaporated. There was thus obtained the required starting material as an oil (0.5 g) which crystallised on standing and was used without further purification.

EXAMPLE 9

The procedure described in Example 5 was repeated except that (2RS,4SR)-4-(3,5-difluorophenyl)-4-methoxy-2-methyltetrahydropyran was used in place of 4-(3,5-difluorophenyl)-4-methoxytetrahydropyran. There was thus obtained (2RS,4SR)-4-[5-fluoro-3-(4-methyl-3-oxo-2,3-dihydro-4H-1,4-benzoxazin-7-ylthio)-phenyl]-4-methoxy-2-methyltetrahydropyran in 20% yield, m.p. 110°–112° C.

NMR Spectrum (CDCl₃, δ values) 1.20 (d, 3H), 1.5–2.15 (m, 4H), 2.98 (s, 3H), 3.37 (s, 3H), 3.75–4.10 (m, 3H), 4.63 (s, 2H), 6.75–7.25 (m, 6H).

The (2RS,4SR)-4-(3,5-difluorophenyl)-4-methoxy-2-methyltetrahydropyran used as a starting material was obtained as follows:

A Grignard reagent was prepared from 3,5-difluorobromobenzene (0.772 g), 1,2-dibromoethane (2 drops), magnesium (0.106 g) and THF (5 ml). The mixture was stirred at ambient temperature for 15 minutes and then heated to 50° C. for 15 minutes. The mixture was allowed to recool to ambient temperature and a solution of 2-methyltetrahydropyran-4-one (*J. Amer. Chem. Soc.*, 1982, 104, 4666) in THF (1 ml) was added dropwise. The mixture was stirred at ambient temperature for 1 hour. The mixture was poured into dilute aqueous hydrochloric acid and extracted with diethyl ether. The organic phase was washed with brine, dried (MgSO₄) and evaporated. The residue was purified by column chromatography using a 9:1 v/v mixture of methylene chloride and diethyl ether as eluent. There was thus obtained a less polar isomer, (2RS,4SR)-4-(3,5-difluorophenyl)-4-hydroxy-2-methyltetrahydropyran (0.25 g, 36%), having the 2-methyl and 4-hydroxy substituents in a trans-relationship.

Sodium hydride (50% w/w dispersion in mineral oil, 0.053 g) was added to a mixture of the product so obtained, methyl iodide (0.233 g) and DMF (3 ml). The mixture was stirred at ambient temperature for 30 minutes. The mixture was acidified to pH3 by the addition of N hydrochloric acid solution and extracted with diethyl ether. The organic phase was washed with water and with brine, dried (MgSO₄) and evaporated. The residue was purified by column chromatography using a 19:1 v/v mixture of methylene chloride and diethyl ether as eluent. There was thus obtained the required starting material (0.23 g, 87%) as an oil.

EXAMPLE 10

The procedure described in Example 5 was repeated except that (2S,4R)-4-(3,5-difluorophenyl)-4-methoxy-2-methyltetrahydropyran was used in place of 4-(3,5-difluorophenyl)-4-methoxytetrahydropyran. There was thus obtained (2S,4R)-4-[5-fluoro-3-(4-methyl-3-oxo-2,3-dihydro-4H-1,4-benzoxazin-7-ylthio)phenyl]-4-methoxy-2-methyltetrahydropyran in 16% yield, m.p. 115°–117° C.

The (2S,4R)-4-(3,5-difluorophenyl)-4-methoxy-2-methyltetrahydropyran used as a starting material was obtained using the procedures described in the portion of Example 9 which is concerned with the preparation of starting materials except that (2S)-2-methyltetrahydropyran-4-one [European Patent Application No. 0385662 (Example 20 thereof)] was used in place of the racemic compound i.e. (2SR)-2-methyltetrahydropyrane-4-one. There was thus obtained the required starting material in 18% yield as an oil.

EXAMPLE 11

A mixture of 7-bromo-4-methyl-2,3-dihydro-4H-pyrido-[3,2-b][1,4]oxazin-3-one (0.244 g), 4-(3-mercaptophenyl)-4-methoxytetrahydropyran (0.224 g), potassium carbonate (0.223 g), cuprous chloride (0.029 g) and DMF (1.1 ml) was heated to 140° C. for 5 hours. The mixture was cooled to ambient temperature and partitioned between ethyl acetate and water. The organic phase was washed with water and with brine, dried (MgSO₄) and evaporated. The residue was purified by column chromatography using a 1:1 v/v mixture of hexane and ethyl acetate as eluent. There was thus obtained 4-methoxy-4-[3-(4-methyl-3-oxo-2,3-dihydro-4H-pyrido[3,2-b][1,4]oxazin-7-ylthio)phenyl]tetrahydropyran (0.1 g, 26%), m.p. 118°–120° C.

The 7-bromo-4-methyl-2,3-dihydro-4H-pyrido-[3,2-b][1,4]oxazin-3-one used as a starting material was obtained as follows:

2,3-Dihydro-4H-pyrido[3,2-b][1,4]oxazin-3-one (U.S. Pat. No. 3,854,926; 1.5 g) was added portionwise to a stirred suspension of sodium hydride (60% w/w dispersion in mineral oil; 0.4 g) in DMF (30 ml) which had been cooled in an ice-bath. The mixture was allowed to warm to ambient temperature and was stirred for 30 minutes. Methyl iodide (0.65 ml) was added and the mixture was stirred at ambient temperature for 16 hours. The mixture was poured into a saturated aqeuous ammonium chloride solution and extracted with ethyl acetate. The organic phase was washed with water and with brine, dried (MgSO₄) and evaporated to give 4-methyl-2,3-dihydro-4H-pyrido[3,2-b][1,4]oxazin-3-one (1.58 g) which was used without further purification.

A mixture of a portion (0.9 g) of the material so obtained, N-bromosuccinimide (1.2 g) and DMF (19 ml) was stirred at ambient temperature for 24 hours. Water (6 ml) was added and the mixture was cooled in an ice-bath. The precipitate (0.3 g) was isolated and dried. The filtrate was partitioned between ethyl acetate and a saturated aqueous ammonium chloride solution. The organic phase was washed with water, with an aqueous sodium thiosulphate solution and with brine, dried (MgSO₄) and evaporated. The residue was purified by column chromatography using a 19:1 v/v mixture of toluene and ethyl acetate as eluent. The product so obtained was combined with the isolated precipitate giving the required starting material (0.46 g, 34%) as a solid.

EXAMPLE 12

Sodium hydride (60% w/w dispersion in mineral oil; 0.021 g) was added portionwise to a stirred mixture of 4-[5-fluoro-3-(3-oxo-2,3-dihydro-4H-1,4-benzoxazin-7-yloxy)phenyl]-4-methoxytetrahydropyran (0.19 g), methyl iodide (0.109 g) and N-methylpyrrolidin-2-one (2 ml) and the mixture was stirred at ambient temperature for 1 hour. The mixture was partitioned between ethyl acetate and water. The organic phase was washed with water, dried (MgSO$_4$) and evaporated. The residue was purified by column chromatography using a 9:1 v/v mixture of methylene chloride and diethyl ether as eluent. There was thus obtained 4-[5-fluoro-3-(4-methyl-3-oxo-2,3-dihydro-4H-1,4-benzoxazin-7-yloxy)-phenyl]-4-methoxytetrahydropyran (0.12 g, 67%) as an oil which crystallised on trituration under a mixture of hexane and diethyl ether, m.p. 108°–109° C.

The 4-[5-fluoro-3-(3-oxo-2,3-dihydro-4H-1,4-benzoxazin-7-yloxy)phenyl]-4-methoxytetrahydropyran, used as a starting material, was obtained as follows:

Sodium hydride (60% w/w dispersion in mineral oil; 0.088 g) was added portionwise to a stirred mixture of ethyl 2-(5-fluoro-2-nitrophenoxy)acetate (0.486 g), 4-(5-fluoro-3-hydroxyphenyl)-4-methoxytetrahydropyran (0.452 g) and N-methylpyrrolidin-2-one (10 ml) and the mixture was stirred at ambient temperature for 5 hours and then heated to 60° C. for 10 hours. The mixture was cooled to ambient temperature and partitioned between diethyl ether and water. The organic phase was washed with a saturated aqueous sodium bicarbonate solution and with water, dried (MgSO$_4$) and evaporated. The residue was purified by column chromatography using a 9:1 v/v mixture of methylene chloride and diethyl ether as eluent. There was thus obtained 4-[5-fluoro-3-(3-ethoxycarbonylmethoxy-4-nitrophenoxy)phenyl]-4-methoxytetrahydropyran (0.32 g, 35%) as an oil.

A mixture of the product so obtained (0.315 g), palladium-on-charcoal catalyst (10% w/v, 0.1 g), methanol (5 ml) and ethyl acetate (3 ml) was stirred at ambient temperature under a pressure of four atmospheres of hydrogen gas for 3 hours. The mixture was filtered and the filtrate was evaporated. There was thus obtained the required starting material (0.19 g, 73%) as a solid which was used without further purification.

EXAMPLE 13

Using the procedure described in Example 12, 4-[5-fluoro-3-(3-oxo-2,3-dihydro-4H-1,4-benzothiazin-7-ylthio)phenyl]-4-methoxytetrahydropyran was reacted with methyl iodide to give 4-[5-fluoro-3-(4-methyl-3-oxo-2,3-dihydro-4H-1,4-benzothiazin-7-ylthio)phenyl]-4-methoxytetrahydropyran in 41% yield, m.p. 131°–133° C.

The 4-[5-fluoro-3-oxo-2,3-dihydro-4H-1,4-benzothiazin-7-ylthio)phenyl]-4-methoxytetrahydropyran, used as a starting material, was obtained as follows:

A solution of ethyl thioglycolate (13.2 g) in bis(2-methoxyethyl) ether (50 ml) was added dropwise to a mixture of 2,4-difluoronitrobenzene (15.9 g), lithium hydroxide monohydrate (4.83 g) and N-methylpyrrolidin-2-one (150 ml) which was cooled in a water bath. The mixture was stirred at ambient temperature for 45 minutes. Water (200 ml) was added and the mixture was acidified to pH5 by the addition of dilute aqueous hydrochloric acid. The mixture was extracted with diethyl ether (3×150 ml). The combined extracts were washed with water and with brine, dried (MgSO$_4$) and evaporated. The residue was purified by column chromatography using a 1:1 v/v mixture of petroleum ether (b.p. 40°–60° C.) and diethyl ether as eluent. There was thus obtained ethyl 2-(5-fluoro-2-nitrophenylthio)acetate (8.9 g, 29%) as an oil which crystallised on trituration under a mixture of hexane and diethyl ether.

Lithium hydroxide monohydrate (0.063 g) was added portionwise to a stirred mixture of ethyl 2-(5-fluoro-2-nitrophenylthio)acetate (0.401 g), 4-(5-fluoro-3-mercaptophenyl)-4-methoxytetrahydropyran (European Patent Application No. 0420511, Example 4 thereof; 0.363 g) and N-methylpyrrolidin-2-one (4 ml). The mixture was stirred at ambient temperature for 2 hours. The mixture was partitioned between diethyl ether and water. The organic phase was washed with water and with brine, dried (MgSO$_4$) and evaporated. The residue was purified by column chromatography using a 19:1 v/v mixture of methylene chloride and diethyl ether as eluent. There was thus obtained 4-[5-fluoro-3-(3-ethoxycarbonylmethylthio-4-nitrophenylthio)phenyl]-4-methoxytetrahydropyran (0.61 g, 87%) as an oil which crystallised on trituration under a mixture of hexane and diethyl ether.

Zinc (0.715 g) was added portionwise to a mixture of the product so obtained (0.529 g), water (1.5 ml) and acetic acid (14 ml) and the mixture was heated to 70° C. for 30 minutes. The mixture was filtered and the filtrate was evaporated. The residue was purified by column chromatography using a 1:1 v/v mixture of methylene chloride and diethyl ether as eluent. There was thus obtained the required starting material as an oil which crystallised on trituration under diethy ether to furnish a solid (0.3 g, 67%), m.p. 151°–152° C.

EXAMPLE 14

Using the procedure described in Example 11, 7-bromo-4-methyl-2,3-dihydro-4H-pyrido[3,2-b][1,4]oxazin-3-one was reacted with 4-(5-fluoro-3-mercaptophenyl)-4-methoxytetrahydropyran to give 4-[5-fluoro-3-(4-methyl-3-oxo-2,3-dihydro-4H-pyrido[3,2-b][1,4]oxazin-7-ylthio)phenyl]-4-methoxytetrahydropyran in 4% yield, m.p. 127°–128° C.

EXAMPLE 15

A solution of 4-[5-fluoro-3-(2,2-dimethyl-3-oxo-2,3-dihydro-4H-1,4-benzoxazin-7-ylthio)phenyl]-4-methoxytetrahydropyran (0.21 g) in DMF (2 ml) was added dropwise to a stirred suspension of sodium hydride (50% w/w dispersion in mineral oil, 0.03 g) in DMF (0.3 ml) and the mixture was stirred at ambient temperature for 20 minutes. Methyl iodide (0.4 ml) was added the mixture was stirred for 1 hour. The mixture was partitioned between diethyl ether and water. The organic phase was washed with water, dried (MgSO$_4$) and evaporated. The residue was purified by column chromatography using a 1:1 v/v mixture of hexane and ethyl acetate as eluent. There was thus obtained 4-[5-fluoro-3-(2,2,4-trimethyl-3-oxo-2,3-dihydro-4H-1,4-benzoxazin-7-ylthio)phenyl]-4-methoxytetrahydropyran (0.15 g, 70%), m.p. 116°–118° C.

The 4-[5-fluoro-3-(2,2-dimethyl-3-oxo-2,3-dihydro-4H-1,4-benzoxazin-7-ylthio)phenyl]-4-methoxytetrahydropyran, used as a starting material, was obtained as follows:

A mixture of 5-fluoro-2-nitrophenol (3.14 g), methyl 2-bromo-2-methylpropionate (3.6 g), potassium carbonate (4.1 g) and DMF (20 ml) was heated to 120° C. for 2 hours. The mixture was partitioned between diethyl ether and water. The organic layer was washed with water, dried (MgSO₄) and evaporated. The residue was purified by column chromatography using a 19:1 v/v mixture of hexane and ethyl acetate as eluent. There was thus obtained methyl 2-methyl-2-(5-fluoro-2-nitrophenoxy)propionate (1.5 g, 28%) as an oil.

A mixture of a portion (1.33 g) of the product so obtained, potassium carbonate (1.3 g), 4-(5-fluoro-3-mercaptophenyl)-4-methoxytetrahydropyran (1.2 g) and DMF (10 ml) was stirred and heated to 80° C. for 1.5 hours. The mixture was cooled to ambient temperature and partitioned between diethyl ether and water. The organic phase was washed with water, dried (MgSO₄) and evaporated. The residue was purified by column chromatography using a 3:1 v/v mixture of hexane and ethyl acetate as eluent. There was thus obtained 4-[5-fluoro-3-(3-(2-methoxycarbonylprop-2-yl)oxy-4-nitrophenylthio)phenyl]-4-methoxytetrahydropyran (2.4 g, 89%), as an oil.

A mixture of a portion (0.48 g) of the product so obtained, 30% palladium-on-charcoal (0.4 g) and ethyl acetate (10 ml) was stirred under an atmosphere of hydrogen for 16 hours. The mixture was filtered and the filtrate was evaporated. The residue was purified by column chromatography using a 1:1 v/v mixture of hexane and ethyl acetate as eluent. There was thus obtained the required starting material (0.24 g, 57%), m.p. 130°–133° C.

EXAMPLE 16

A solution of (S)-(+)-4-[5-fluoro-3-(2-methyl-3-oxo-2,3-dihydro-4H-1,4-benzoxazin-7-ylthio)phenyl]-4-methoxytetrahydropyran (0.18 g) in DMF (5 ml) was added dropwise to a stirred suspension of sodium hydride (60% w/w dispersion in mineral oil, 0.018 g) in DMF (2 ml) which had been cooled to 10° C. The mixture was stirred at ambient temperature for 30 minutes. Methyl iodide (0.077 g) was added and the mixture was stirred at ambient temperature for 1 hour. The mixture was partitioned between water and ethyl acetate. The organic phase was washed with water, dried (MgSO₄) and evaporated. The residue was purified by column chromatography using a 1:1 v/v mixture of hexane and ethyl acetate as eluent. There was thus obtained (S)-(+)-4-[5-fluoro-3-(2,4-dimethyl-3-oxo-2,3-dihydro-4H-1,4-benzoxazin-7-ylthio)phenyl]-4-methoxytetrahydropyran (0.124 g, 66%), m.p. 104°–106° C.

Specific Rotation: [alpha]$_D$= +39° (methylene chloride, c=1 g/100 ml, temp. =25° C.)

The (S)-(+)-4-[5-fluoro-3-(2-methyl-3-oxo-2,3-dihydro-4H-1,4-benzoxazin-7-ylthio)phenyl]-4-methoxytetrahydropyran, used as a starting material, was obtained as follows:

A mixture of 5-fluoro-2-nitrophenol (0.47 g), (R)-(+)-methyl 2-chloropropionate (0.37 g), potassium carbonate (0.621 g) and DMF (10 ml) was heated to 60° C. for 18 hours. The mixture was partitioned between ethyl acetate and water. The organic layer was washed with water, dried (MgSO₄) and evaporated. There was thus obtained (S)-(+)-methyl 2-(5-fluoro-2-nitrophenoxy)propionate (0.453 g, 62%), m.p. 50°–52° C.

Specific Rotation: [alpha]$_D$= +40.2° (methylene chloride, c=1 g/100 ml).

A mixture of a portion (0.4 g) of the product so obtained, potassium carbonate (0.33 g), 4-(5-fluoro-3-mercaptophenyl)-4-methoxytetrahydropyran (0.39 g) and DMF (5 ml) was stirred and heated to 85° C. for 3 hours. The mixture was cooled to ambient temperature and partitioned between ethyl acetate and water. The organic phase was washed with water, dried (MgSO₄) and evaporated. The residue was purified by column chromatography using a 3:1 v/v mixture of hexane and ethyl acetate as eluent. There was thus obtained (S)-4-[5-fluoro-3-(3-(1-methoxycarbonyl)ethoxy)-4-nitrophenylthio)phenyl]-4-methoxytetrahydropyran (0.558 g, 75%), as an oil.

A mixture of a portion (0.314 g) of the product so obtained, iron filings (1.135 g), ferrous sulphate heptahydrate (0.192 g) and methanol (25 ml) was stirred vigorously and heated to reflux for 4 hours. The mixture was cooled to ambient temperature and filtered. The residue was washed with methylene chloride. The combined filtrates were washed with water, dried (MgSO₄) and evaporated. The residue was purified by column chromatography using a 1:1 v/v mixture of hexane and ethyl acetate as eluent. There was thus obtained the required starting material (0.238 g, 84%) as an oily solid.

NMR Spectrum (CDCl₃, δ values) 1.59 (d, 3H), 1.89 (m, 4H), 2.98 (s, 3H), 3.8 (m, 4H), 4.7 (q, 1H), 6.8–7.1 (m, 6H), 8.4 (broad hump, 1H).

EXAMPLE 17

Using a similar procedure to that described in Example 16, (R)-(−)-4-[5-fluoro-3-(2-methyl-3-oxo-2,3-dihydro-4H-1,4-benzoxazin-7-ylthio)phenyl]-4-methoxytetrahydropyran was reacted with methyl iodide to give (R)-(−)-4-[5-fluoro-3-(2,4-dimethyl-3-oxo-2,3-dihydro-4H-1,4-benzoxazin-7-ylthio)phenyl]-4-methoxytetrahydropyran in 42% yield, m.p. 107°–109° C.

Specific Rotation: [alpha]$_D$= −36.8° (methylene chloride, c=1 g/100 ml, temp.=25° C.).

The (R)-(−)-4-[5-fluoro-3-(2-methyl-3-oxo-2,3-dihydro-4H-1,4-benzoxazin-7-ylthio)phenyl]-4-methoxytetrahydropyran, used as a starting materials, was obtained by the same procedure as that described in the portion of Example 16 which is concerned with the preparation of starting materials except that (S)-(−)-methyl 2-chloropropionate was used in place of (R)-(+)-methyl 2-chloropropionate. There was thus obtained the required starting material in 50% yield, m.p. 147°–149° C.

EXAMPLE 18

The following illustrate representative pharmaceutical dosage forms containing the compound of formula I, or a pharmaceutically-acceptable salt thereof (hereafter compound X), for therapeutic or prophylactic use in humans:

(a)
| Tablet I | mg/tablet |
| --- | --- |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

(b)
| Tablet II | |
| --- | --- |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

(c)
| Tablet III | |
| --- | --- |
| Compound X | 1.0 |
| Lactose Ph.Eur | 93.25 |

|     |                                      |                          |
| --- | ------------------------------------ | ------------------------ |
|     | Croscarmellose sodium                | 4.0                      |
|     | Maize starch paste (5% w/v paste)    | 0.75                     |
|     | Magnesium stearate                   | 1.0                      |
| (d) | Capsule                              | mg/capsule               |
|     | Compound X                           | 10                       |
|     | Lactose Ph.Eur                       | 488.5                    |
|     | Magnesium stearate                   | 1.5                      |
| (e) | Injection I                          | (50 mg/ml)               |
|     | Compound X                           | 5.0% w/v                 |
|     | 1M Sodium hydroxide solution         | 15.0% v/v                |
|     | 0.1M Hydrochloric acid               |                          |
|     | (to adjust pH to 7.6)                |                          |
|     | Polyethylene glycol 400              | 4.5% w/v                 |
|     | Water for injection to 100%          |                          |
| (f) | Injection II                         | (10 mg/ml)               |
|     | Compound X                           | 1.0% w/v                 |
|     | Sodium phosphate BP                  | 3.6% w/v                 |
|     | 0.1M Sodium hydroxide solution       | 15.0% v/v                |
|     | Water for injection to 100%          |                          |
| (g) | Injection III                        | (1 mg/ml, buffered to pH 6) |
|     | Compound X                           | 0.1% w/v                 |
|     | Sodium phosphate BP                  | 2.26% w/v                |
|     | Citric acid                          | 0.38% w/v                |
|     | Polyethylene glycol 400              | 3.5% w/v                 |
|     | Water for injection to 100%          |                          |
| (h) | Aerosol I                            | mg/ml                    |
|     | Compound X                           | 10.0                     |
|     | Sorbitan trioleate                   | 13.5                     |
|     | Trichlorofluoromethane               | 910.0                    |
|     | Dichlorodifluoromethane              | 490.0                    |
| (i) | Aerosol II                           |                          |
|     | Compound X                           | 0.2                      |
|     | Sorbitan trioleate                   | 0.27                     |
|     | Trichlorofluoromethane               | 70.0                     |
|     | Dichlorodifluoromethane              | 280.0                    |
|     | Dichlorotetrafluoroethane            | 1094.0                   |
| (j) | Aerosol III                          |                          |
|     | Compound X                           | 2.5                      |
|     | Sorbitan trioleate                   | 3.38                     |
|     | Trichlorofluoromethane               | 67.5                     |
|     | Dichlorodifluoromethane              | 1086.0                   |
|     | Dichlorotetrafluoroethane            | 191.6                    |
| (k) | Aerosol IV                           |                          |
|     | Compound X                           | 2.5                      |
|     | Soya lecithin                        | 2.7                      |
|     | Trichlorofluoromethane               | 67.5                     |
|     | Dichlorodifluoromethane              | 1086.0                   |
|     | Dichlorotetrafluoroethane            | 191.6                    |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

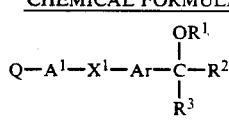

I

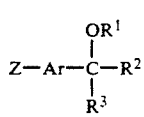

II

CHEMICAL FORMULAE

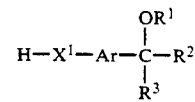

III

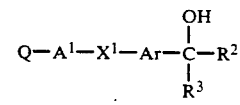

IV

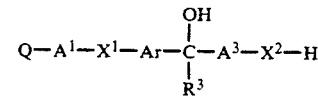

V

SCHEME I

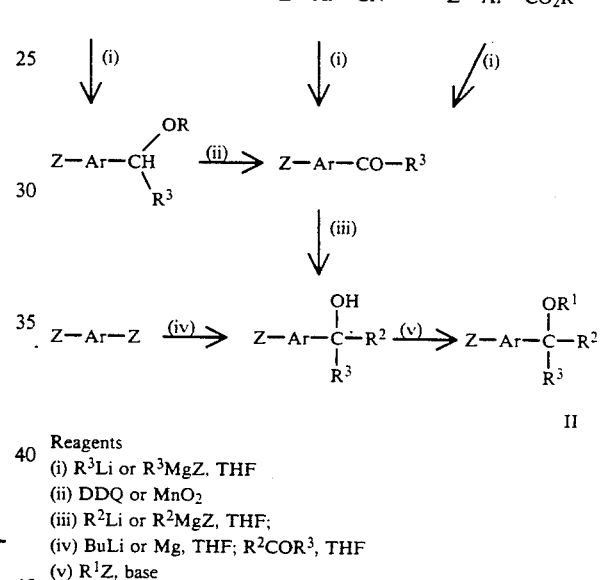

Reagents
(i) $R^3Li$ or $R^3MgZ$, THF
(ii) DDQ or $MnO_2$
(iii) $R^2Li$ or $R^2MgZ$, THF;
(iv) BuLi or Mg, THF; $R^2COR^3$, THF
(v) $R^1Z$, base
Note R = (1–4C)alkyl such as Me or Et

SCHEME II

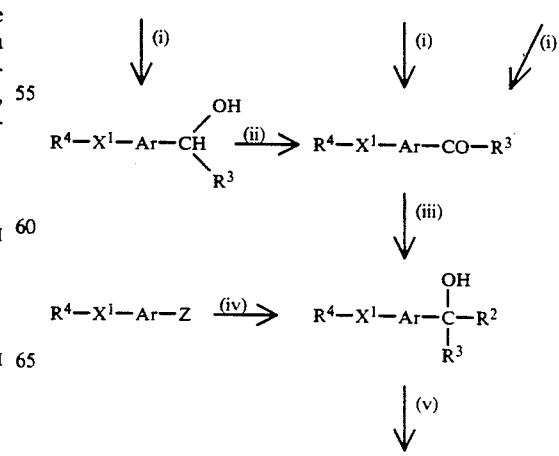

-continued
SCHEME II

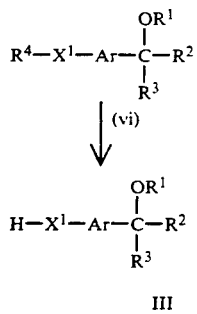

Reagants
(i) to (v) as in Scheme I
(vi) Conventional removal of the protecting group $R^4$ which is, e.g. COMe, THP, CH$_2$Ph or Me.

SCHEME III

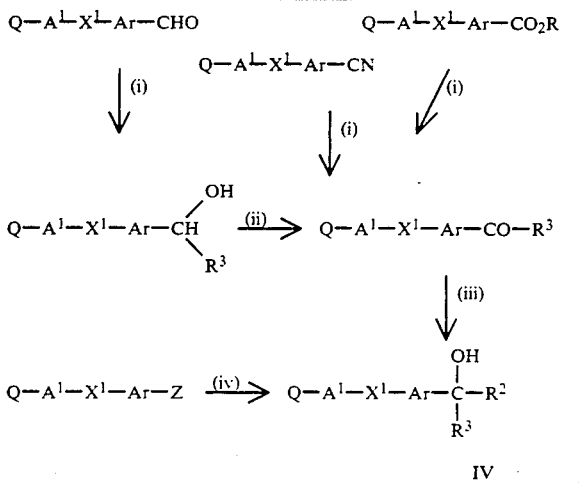

Reagents
(i) to (iv) as in Scheme I

SCHEME IV

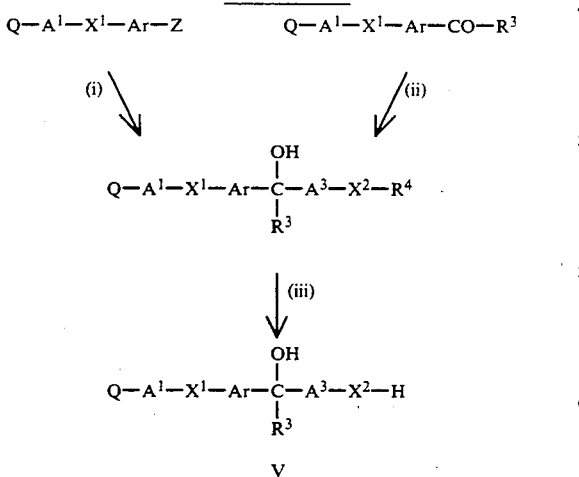

Reagents
(i) BuLi or Mg, THF; $R^3$—CO—$A^3$—$X^2$—$R^4$
(ii) $R^4$—$X^2$—$A^3$—Li or $R^4$—$X^2$—$A^3$—MgZ, THF
(iii) Conventional removal of the protecting group $R^4$ which is, e.g. COMe, THP, CH$_2$Ph or Me.

What we claim is:
1. A bicyclic heterocyclic compound of the formula I

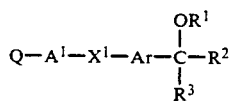

wherein Q is a benzoxazinyl or a hydrogenated derivative thereof which may optionally bear one or two oxo or thioxo substituents and up to four further substituents selected from halogeno, hydroxy, cyano, amino, (1–4-C)alkyl, (1–4C)alkoxy, fluoro-(1–4C)alkyl, (1–4C)alkylamino, di-[(1–4C)alkyl]amino, amino-(1–4C)alkyl, (1–4C)alkylamino-(1–4C)alkyl, di-[(1–4C)alkyl]amino-(1–4C)alkyl, phenyl and phenyl-(1–4C)alkyl, and wherein said phenyl or phenyl-(1–4C)alkyl substituent may optionally bear a substituent selected from halogeno, (1–4C)alkyl and (1–4C)alkoxy;

wherein $A^1$ is a direct link to $X^1$ or is (1–3C)alkylene;
wherein $X^1$ is oxy, thio, sulphinyl, sulphonyl or imino;
wherein Ar is phenylene which may optionally bear one or two substituents selected from halogeno, hydroxy, amino, nitro, cyano, carbamoyl, ureido, (1–4C)alkyl, (1–4C)alkoxy, (1–4C)alkylamino, di-[(1–4C)alkyl]amino, fluoro-(1–4C)alkyl and (2–4C)alkanoylamino; or
Ar is pyridylene;
wherein $R^1$ is (1–4C)alkyl, (3–4C)alkenyl or (3–4C)alkynyl; and
wherein $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ and $A^3$, which may be the same or different, each is (1–3)alkylene and $X^2$ is oxy, and which ring may bear one, two or three substituents, which may be the same or different, selected from hydroxy, (1–4C)alkyl and (1–4C)alkoxy; or wherein $R^1$ and $R^2$ together form a group of the formula —$A^2$—$X^2$—$A^3$— which, together with the oxygen atom to which $A^2$ is attached and with the carbon atoms to which $A^3$ is attached, defines a ring having 5 or 6 ring atoms, wherein $A^2$ and $A^3$, which may be the same or different, each is (1–3C)alkylene and $X^2$ is oxy, and which ring may bear one, two or three (1–4C)alkyl substituents, and wherein $R^3$ is (1–4C)alkyl, (2–4C)alkenyl or (2–4C)alkynyl; or a pharmaceutically-acceptable salt thereof.

2. A bicyclic heterocyclic compound of the formula I as claimed in claim 1
wherein Q is 4H-1,4-benzoxazinyl or the corresponding 2,3-dihydro derivatives thereof, which may optionally bear one oxo or thioxo substituent and up to four substituents selected from fluoro, chloro, bromo, hydroxy, cyano, amino, methyl, ethyl, propyl, methoxy, trifluoromethyl, 2-fluoroethyl, 2,2,2-trifluoroethyl, 2-methylaminoethyl, 2-dimethylaminoethyl, phenyl and benzyl, and wherein said phenyl or benzyl substituent may optionally bear a substituent selected from chloro, methyl and methoxy;
$A^1$ is a direct link to $X^1$ or is methylene;
$X^1$ is oxy, thio, sulphinyl or sulphonyl;

Ar is 1,3-phenylene or 1,4-phenylene which may optionally bear one or two substituents selected from fluoro, chloro, hydroxy, amino, nitro, ureido, methoxy, dimethylamino, trifluoromethyl and acetamido; or Ar is 3,5-pyridylene;

$R^1$ is methyl, ethyl, allyl or 2-propynyl; and $R^2$ and $R^3$ together form of a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl, ethyl, propyl, methoxy and ethoxy;

or $R^1$ and $R^2$ together form a group of the formula $-A^2-X^2-A^3-$ which, together with the oxygen atom to which $A^2$ is attached and with the carbon atom to which $A^3$ is attached, defines a ring having 5 or 6 ring atoms, wherein $A^2$ is methylene, $A^3$ is methylene or ethylene, and $X^2$ is oxy, and which ring may bear one, two or three substituents selected from methyl, ethyl and propyl, and $R^3$ is methyl or ethyl; or a pharmaceutically-acceptable salt thereof.

3. A bicyclic heterocyclic compound of the formula I wherein Q is 3-oxo-2,3-dihydro-4H-1,4-benzoxazin-7-yl which may optionally bear one, two or three substituents selected from fluoro, chloro, methyl, ethyl, propyl, 2-fluoroethyl, 2-dimethylaminoethyl, phenyl and benzyl;

$A^1$ is a direct link to $X^1$, or is methylene;

$X^1$ is oxy, thio, sulphinyl or sulphonyl;

Ar is 1,3-phenylene or 1,4-phenylene which may optionally bear one or two substituents selected from fluoro, hydroxy, amino, nitro, ureido, methoxy, dimethylamino, trifluoromethyl and acetamido; or Ar is 3,5-pyridylene;

$R^1$ is methyl, ethyl, allyl or 2-propynyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or $R^1$ and $R^2$ together form a group of the formula $-A^2-X^2-A^3-$ which, together with the oxygen atom to which $A^2$ is attached and with the carbon atom to which $A^3$ is attached, defines a ring having 5 ring atoms, wherein $A^2$ is methylene, $A^3$ is methylene, and $X^2$ is oxy, and which ring may bear one, two or three substituents selected from methyl and ethyl, and $R^3$ is methyl or ethyl; or a pharmaceutically-acceptable salt thereof.

4. A bicyclic heterocyclic compound of the formula I as claimed in claim 1 wherein Q is 3-oxo-2,3-dihydro-4H-1,4-benzoxazin-7-yl or the corresponding 4-methyl derivative thereof, which may optionally bear one or two substituents selected from methyl and ethyl;

$A^1$ is a direct link to $X^1$, or is methylene;

$X^1$ is oxy, thio, sulphinyl or sulphonyl;

Ar is 1,3-phenylene which may optionally bear one or two substituents selected from fluoro, methoxy and trifluoromethyl;

$R^1$ is methyl, ethyl or allyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl, ethyl, propyl and methoxy; or a pharmaceutically-acceptable salt thereof.

5. A bicyclic heterocyclic compound of the formula I as claimed in claim 1 wherein Q is 4-methyl-3-oxo-2,3-dihydro-4H-1,4-benzoxazin-7-yl or the corresponding 2,2-dimethyl derivative thereof;

$A^1$ is methylene;

$X^1$ is oxy;

Ar is 1,3-phenylene or 5-fluoro-1,3-phenylene;

$R^1$ is methyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

or a pharmaceutically-acceptable salt thereof.

6. A bicyclic heterocyclic compound of the formula I as claimed in claim 1 wherein Q is 3-oxo-2,3-dihydro-4H-1,4-benzoxazin-6-yl, 3-oxo-2,3-dihydro-4H-1,4-benzoxazin-7-yl, 3-thioxo-2,3-dihydro-4H-1,4-benzoxazin-7-yl or 2-oxo-1,2-dihydro-4H-3,1-benzoxazin-6-yl or the corresponding N-methyl derivatives thereof, which may optionally bear one or two substituents selected from methyl and ethyl;

$A^1$ is a direct link to $X^1$, or is methylene;

$X^1$ is oxy, thio, sulphinyl or sulphonyl;

Ar is 1,3-phenylene which may optionally bear one or two substituents selected from fluoro, methoxy and trifluoromethyl;

$R^1$ is methyl, ethyl or allyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected form methyl, ethyl, propyl and methoxy; or a pharmaceutically-acceptable salt thereof.

7. A bicyclic heterocyclic compound of the formula I as claimed in claim 1 wherein Q is 4-methyl-3-oxo-2,3-dihydro-4H-1,4-benzoxazin-6-yl, 4-methyl-3-oxo-2,3-dihydro-4H-1,4-benzoxazin-7-yl, 2,2,4-trimethyl-3-oxo-2,3-dihydro-4H-1,4-benzoxazin-7-yl, 4-methyl-3-thioxo-2,3-dihydro-4H-1,4-benzoxazin-7-yl or 1-methyl-2-oxo-1,2-dihydro-4H-3,1-benzoxazin-6-yl;

$A^1$ is a direct link to $X^1$, or is methylene;

$X^1$ is oxy or thio;

Ar is 1,3-phenylene or 5-fluoro-1,3-phenylene;

$R^1$ is methyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

or a pharmaceutically-acceptable salt thereof.

8. A bicyclic heterocyclic compound of the formula I, or a pharmaceutically-acceptable salt thereof as defined in claim 1, selected from the group consisting of:

4-[5-fluoro-3-(4-methyl-3-oxo-2,3-dihydro-4H-1,4-benzoxazin-7-ylmethoxy)phenyl]-4-methoxytetrahydropyran, and 4-[5-fluoro-3-(2,2,4-trimethyl-3-oxo-2,3-dihydro-4H-1,4-benzoxazin-7-ylmethoxy)-phenyl]-4-methoxytetrahydropyran.

9. A bicyclic heterocyclic compound of the formula I, or a pharmaceutically-acceptable salt thereof as defined in claim 1 and selected from the group consisting of:

4-[5-fluoro-3-(4-methyl-3-thioxo-2,3-dihydro-4H-1,4-benzoxazin-7-ylthio)phenyl]4-methoxytetrahydropyran;

4-[5-fluoro-3-(4-methyl-3-oxo-2,3-dihydro-4H-1,4-benzoxazin-7-ylthio)phenyl]-4-methoxytetrahydropyran;

(2S,4R)-4-[5-fluoro-3-(4-methyl-3-oxo-2,3-dihydro-4H-1,4-benzoxazin-7-ylthio)phenyl]-4-methoxy-2-methyltetrahydropyran;

(S)-(+)-4-[5-fluoro-3-(2,4-dimethyl-3-oxo-2,3-dihydro-4H-1,4-benzoxazin-7-ylthio)phenyl]-4-methoxytetrahydropyran and (R)-(−)-4-[5-fluoro-3-(2,4-dimethyl-3-oxo-2,3-dihydro-4H-1,4-benzoxazin-7-ylthio)phenyl]-4-methoxytetrahydropyran.

10. A pharmaceutical composition which comprises a bicyclic heterocyclic compound of the formula I, or a pharmaceutically-acceptable salt thereof, as claimed in any one of claims 1 to 9 in association with a pharmaceutically-acceptable diluent or carrier.

11. A method of treating a disease or medical condition mediated alone or in part by one or more leukotrienes which comprises administering to a warm-blooded animal requiring such treatment an effective amount of a bicyclic heterocyclic compound of the formula I, or a pharmaceutically-acceptable salt thereof, as claimed in any one of claims 1 to 9.

12. A pharmaceutical composition which comprises a bicyclic heterocyclic compound of the formula I, or a pharmaceutically-acceptable salt thereof, as claimed in any one of claims 1 to 9 in conjunction or admixture whith a cyclooxygenase inhibitory non-steroidal anti-inflammatory agent; and a pharmaceutically-acceptable diluent or carrier.

* * * * *